United States Patent
Kouzuma et al.

(10) Patent No.: US 8,080,423 B2
(45) Date of Patent: Dec. 20, 2011

(54) REAGENT CONTAINING PROTEASE REACTION PROMOTER AND/OR COLORANT STABILIZER

(75) Inventors: Takuji Kouzuma, Mishima (JP); Yoko Nagai, Izunokuni (JP); Shigeyuki Imamura, Izunokuni (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 932 days.

(21) Appl. No.: 11/573,179

(22) PCT Filed: Aug. 4, 2005

(86) PCT No.: PCT/JP2005/014291
§ 371 (c)(1),
(2), (4) Date: Mar. 22, 2007

(87) PCT Pub. No.: WO2006/013921
PCT Pub. Date: Feb. 9, 2006

(65) Prior Publication Data
US 2007/0224685 A1 Sep. 27, 2007

(30) Foreign Application Priority Data

Aug. 5, 2004 (JP) ................. 2004-229498
Sep. 28, 2004 (JP) ................. 2004-281226

(51) Int. Cl.
*G01N 33/72* (2006.01)
(52) U.S. Cl. ............... 436/67; 436/18; 436/63; 436/66; 436/174; 436/176; 436/86; 436/88; 435/23; 435/28
(58) Field of Classification Search .......... 436/8, 18, 436/63, 66, 67, 164, 166, 174, 176, 86, 88; 435/23, 27, 28, 24, 189, 195; 252/408.1; 536/103
See application file for complete search history.

(56) References Cited

U.S. PATENT DOCUMENTS

| | | | |
|---|---|---|---|
| 4,361,108 A | 11/1982 | Angleman et al. | |
| 4,647,532 A | 3/1987 | Watanabe et al. | |
| 4,837,331 A * | 6/1989 | Yamanishi et al. | 548/146 |
| 5,089,420 A | 2/1992 | Albarella et al. | |
| 5,334,382 A * | 8/1994 | Phillips et al. | 424/94.3 |
| 5,370,990 A | 12/1994 | Staniford et al. | |
| 5,792,736 A | 8/1998 | Nakayama et al. | |
| 5,902,731 A | 5/1999 | Ouyang et al. | |
| 6,255,061 B1 | 7/2001 | Mori et al. | |
| 6,352,835 B1 | 3/2002 | Komori et al. | |
| 6,586,199 B2 | 7/2003 | Ouyang et al. | |
| 6,790,665 B2 | 9/2004 | Yonehara et al. | |
| 7,018,823 B2 | 3/2006 | Kurosawa et al. | |
| 7,025,734 B1 * | 4/2006 | Ellis et al. | 600/585 |
| 7,070,948 B1 | 7/2006 | Sakaue et al. | |
| 7,235,378 B2 | 6/2007 | Yonehara | |
| 7,250,269 B2 * | 7/2007 | Kouzuma et al. | 435/25 |
| 2003/0175232 A1 | 9/2003 | Elliott et al. | |
| 2003/0186346 A1 | 10/2003 | Yagi et al. | |
| 2004/0063213 A1 | 4/2004 | Hirai et al. | |
| 2004/0205900 A1 | 10/2004 | Yagi et al. | |
| 2005/0101771 A1 | 5/2005 | Kouzuma et al. | |
| 2005/0130251 A1 | 6/2005 | Okabe et al. | |
| 2005/0221415 A1 | 10/2005 | Yonehara et al. | |
| 2005/0244926 A1 | 11/2005 | Kurosawa et al. | |
| 2005/0260735 A1 | 11/2005 | Yonehara et al. | |
| 2007/0026523 A1 * | 2/2007 | Taniguchi et al. | 436/18 |
| 2007/0037243 A1 | 2/2007 | Hirokawa et al. | |
| 2007/0134754 A1 | 6/2007 | Hirai | |
| 2007/0224685 A1 | 9/2007 | Kouzuma et al. | |
| 2008/0113381 A1 | 5/2008 | Matsuoka et al. | |
| 2008/0241816 A1 | 10/2008 | Taniguchi et al. | |
| 2008/0295259 A1 * | 12/2008 | Ueda et al. | 8/401 |

FOREIGN PATENT DOCUMENTS

| | | |
|---|---|---|
| CN | 1501981 A | 6/2004 |
| EP | 0 439 208 | 7/1991 |
| EP | 0 526 150 | 2/1993 |
| EP | 0729031 | 8/1996 |
| EP | 1 223 224 | 7/2002 |
| EP | 1 308 787 | 5/2003 |
| EP | 1626088 | 2/2004 |
| EP | 1607475 | 12/2005 |
| EP | 1 679 378 | 7/2006 |
| EP | 1 693 461 | 8/2006 |
| EP | 1 693 463 | 8/2006 |
| EP | 1693462 | 8/2006 |
| EP | 1726660 | 11/2006 |
| EP | 1 767 942 | 3/2007 |
| EP | 1 788 081 | 5/2007 |
| EP | 2 108 952 | 10/2009 |
| GB | 2 348 433 | 10/2000 |
| JP | 58187858 | * 11/1983 |
| JP | 60-200167 | 10/1985 |
| JP | 63-243879 | 10/1988 |
| JP | 1-118768 | 5/1989 |
| JP | 4-213064 | 8/1992 |
| JP | 4-262796 | 9/1992 |

(Continued)

OTHER PUBLICATIONS

Kouzuma et al., "An Enzymatic Method for the Measurement of Glycated Albumin in Biological Samples", Clinica Chimica Acta, vol. 324, pp. 61-71 (2002).
I. Sakurabayashi et al., "New Enzymatic Assay for Glycohemoglobin", Clinical Chemistry, vol. 49, No. 2, pp. 269-274 (2003).
English language abstract of JP 2001-204495, Jul. 31, 2001.
English language abstract of JP 2002-315600, Oct. 29, 2002.
English language abstract of JP 1-118768, May 11, 1989.
English language abstract of JP 60-200167, Oct. 9, 1985.
English language abstract of JP 2000-93199, Apr. 4, 2000.
English language abstract of JP 2001-292795, Oct. 23, 2001.

(Continued)

*Primary Examiner* — Maureen Wallenhorst
(74) *Attorney, Agent, or Firm* — Greenblum & Bernstein, PLC

(57) ABSTRACT

Stabilizers for colorants used for detection of enzymatic reactions, having a cyclodextrin and a catalase; reagents including stabilizers; and methods of use of such stabilizers and reagents.

8 Claims, 3 Drawing Sheets

FOREIGN PATENT DOCUMENTS

| | | |
|---|---|---|
| JP | 6-086698 | 3/1994 |
| JP | 6-165696 | 6/1994 |
| JP | 8-089291 | 4/1996 |
| JP | 8-262027 | 10/1996 |
| JP | 11-209795 | 8/1999 |
| JP | 2000-93199 | 4/2000 |
| JP | 3034698 | 4/2000 |
| JP | 2000-175699 | 6/2000 |
| JP | 2000-210100 | 8/2000 |
| JP | 2001-095598 | 4/2001 |
| JP | 2001-204495 | 7/2001 |
| JP | 2001-292795 | 10/2001 |
| JP | 2002-315600 | 10/2002 |
| JP | 2003-232789 | 8/2003 |
| JP | 2003-235585 | 8/2003 |
| JP | 2004-275013 | 10/2004 |
| JP | 2005-110507 | 4/2005 |
| JP | 2005-110657 | 4/2005 |
| JP | 2005-331372 | 12/2005 |
| JP | 2006-340684 | 12/2006 |
| JP | 2007-029094 | 2/2007 |
| WO | 01/18165 | 3/2001 |
| WO | 01/25475 | 4/2001 |
| WO | 02/06519 | 1/2002 |
| WO | 02/21142 | 3/2002 |
| WO | 02/27012 | 4/2002 |
| WO | 02/27330 | 4/2002 |
| WO | 02/27331 | 4/2002 |
| WO | 02/061119 | 8/2002 |
| WO | 03/033601 | 4/2003 |
| WO | 03/107011 | 12/2003 |
| WO | 2004/007760 | 1/2004 |
| WO | 2004/083360 | 9/2004 |
| WO | 2004/104203 | 12/2004 |
| WO | 2005/028660 | 3/2005 |
| WO | 2005/049857 | 6/2005 |
| WO | 2005/049858 | 6/2005 |
| WO | 2005/056823 | 6/2005 |
| WO | 2005/087946 | 9/2005 |
| WO | 2005/088305 | 9/2005 |
| WO | 2005/121795 | 12/2005 |
| WO | 2006/013921 | 2/2006 |
| WO | 2007/083703 | 7/2007 |
| WO | 2008/093722 | 8/2008 |

OTHER PUBLICATIONS

English language abstract of JP 2003-232789, Aug. 22, 2003.
English language abstract of JP 2000-210100, Aug. 2, 2000.
English language abstract of JP 11-209795, Aug. 3, 1999.
English language abstract of JP 8-262027, Oct. 11, 1996.
U.S. Appl. No. 10/557,892 (Matsuoka et al.), filed Nov. 18, 2005 and entitled, "Hemoglobin A1C Determination Method, Enzyme to be Used therefore, and Production Method thereof".
Wiss, "Untersuchung über Proteasen. 1. Aminisäuren, Blausäure and Pyrophosphat asl Effektoren des Pepsin," Helvetica Chimica Acta, vol. 29, pp. 237-246, 1946.
Veierskov et al., "Metabolism of Oat Leaves during Senescence," Plant Physiology, vol. 78, No. 2, pp. 315-319, 1985.
Pillai et al., "Enzymatic Digestion—A Safe and Rapid Technique for Individual Separation of *Macrobrachium rosenbergii* Embryos for Cryopreservation Studies," Cryobiology, vol. 47, No. 3, pp. 242-246, 2003.
Japanese Office Action (Notice for Reasons of Rejection) issued with respect to Japanese Patent App. No. 2005-506428, issued Mar. 10, 2010 (partial English language translation).
Jeppsson et al., *Clinical Chemistry and Laboratory Medicine*, 40(1):78-89 (2002).
Uemoto, *Rinsyokensa* (*Journal of Medical Technology*) 46(7):729-734 (2002), and an English language Abstract of the same.
Japanese Office Action dated Jun. 30, 2010 that issued with respect to Japanese Patent Application No. 2007-041551, along with a partial English language translation thereof.
Office action that issued with respect to patent family member Chinese Patent Application No. 201010255071.8, dated May 12, 2011 along with an english translation thereof.
Japanese Official Action issued with respect to Japanese Patent Application 2006-531538 dated Mar. 17, 2011.

\* cited by examiner

[FIG. 1]
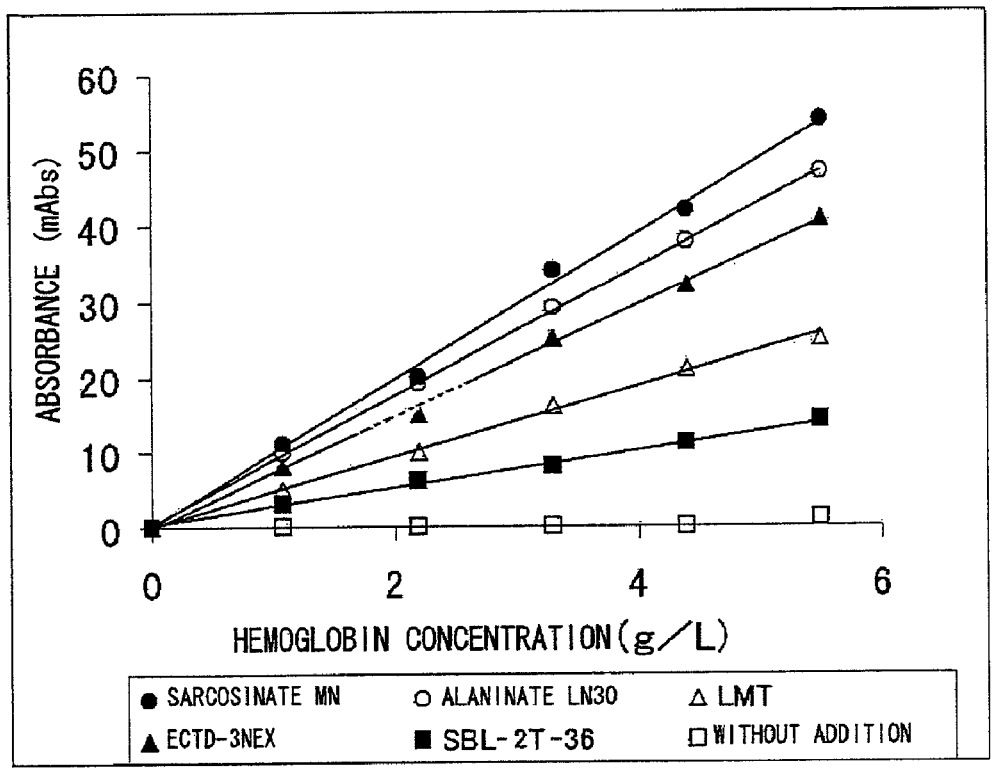
[FIG. 2]
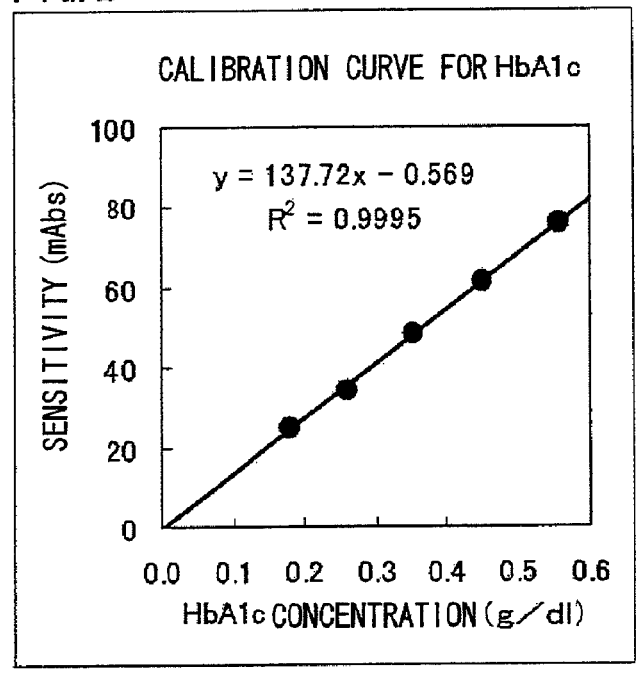

[FIG. 3]
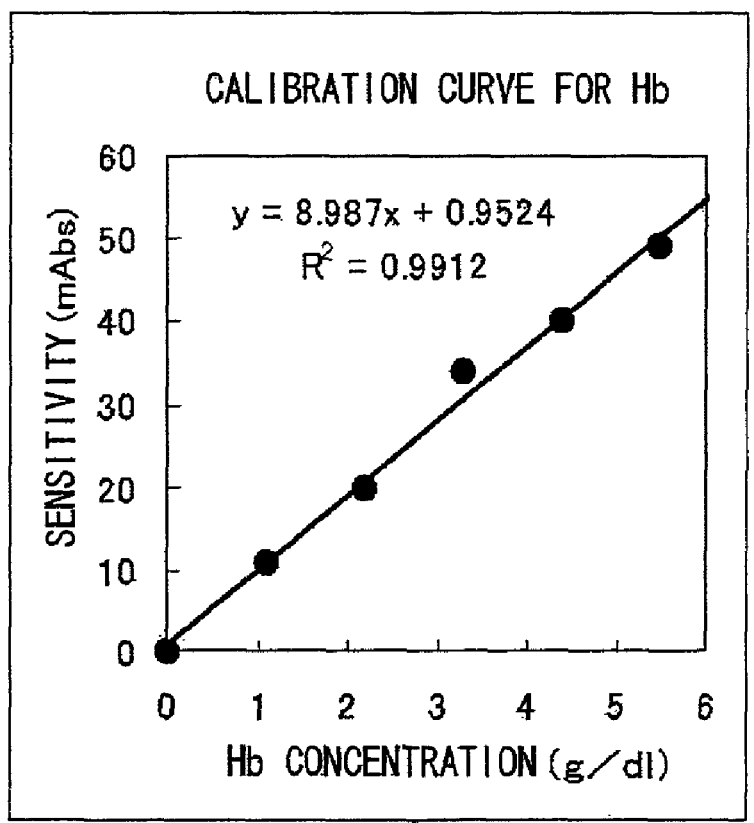
[FIG. 4]
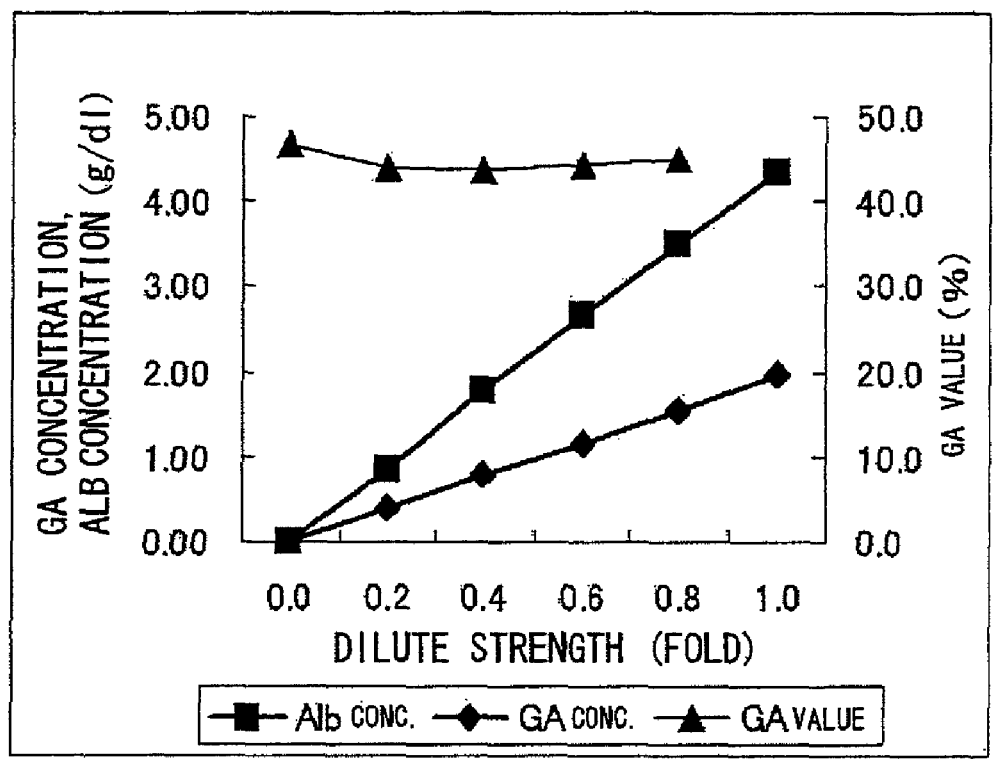

[FIG. 5]
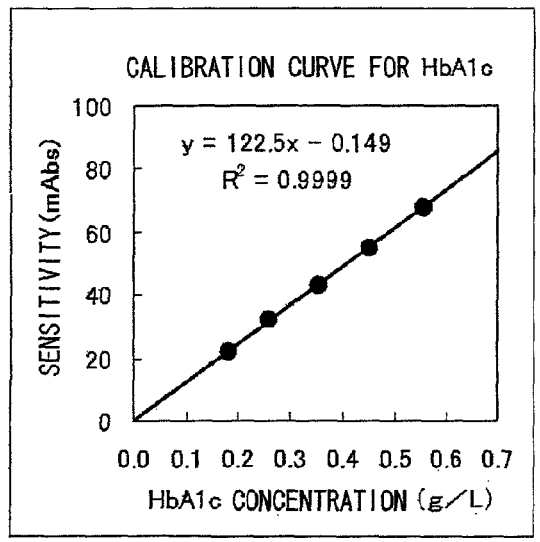
[FIG. 6]
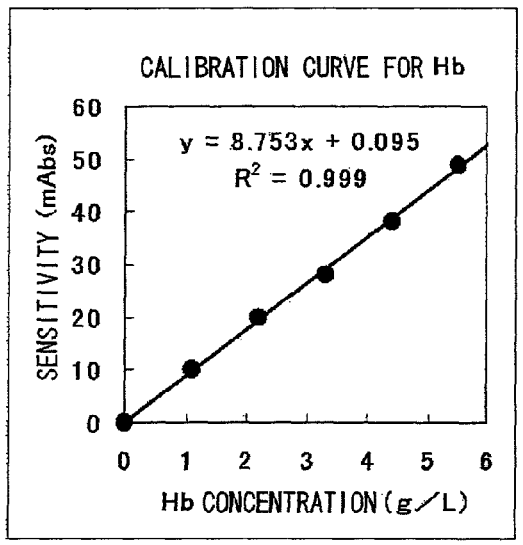
[FIG. 7]
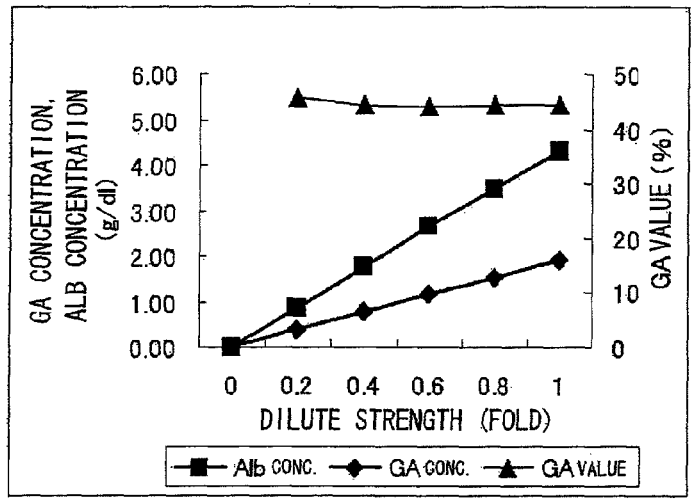

REAGENT CONTAINING PROTEASE REACTION PROMOTER AND/OR COLORANT STABILIZER

TECHNICAL FIELD

The present invention relates to a protease reaction promoter and a method of promoting a protease reaction. In addition, the present invention relates to a reagent containing the protease reaction promoter, and a measurement method using the same. In particular, the present invention relates to a reagent for and a method of measuring hemoglobin, a glycated protein, or a ratio of a glycated protein, which use a protease reaction promoter. Specifically, the present invention relates to a reagent for and a method of quantitatively measuring hemoglobin, hemoglobin A1c, and glycated albumin which are useful for a clinical laboratory test in an accurate, simple, and rapid manner.

Further, the present invention relates to: a stabilizer for a colorant used for detection of an enzymatic reaction, which is characterized by containing a cyclodextrin; a reagent containing a cyclodextrin and the colorant used for the detection of an enzymatic reaction; and a method of stabilizing the colorant used for the detection of an enzymatic reaction. Further, the present invention relates to a reagent for and a method of measuring a glycated protein or a ratio of a glycated protein, which use the colorant stabilized by using a cyclodextrin.

Further, the present invention relates to a reagent for and a method of measuring a glycated protein or a ratio of a glycated protein, which use a protease reaction promoter and a colorant used for detection of an enzymatic reaction which is stabilized by using a cyclodextrin. Specifically, the present invention relates to a reagent for and a method of quantifying glycated hemoglobin, hemoglobin A1c, and glycated albumin which are useful in a clinical laboratory test in an accurate, simple, and rapid manner.

The present application is filed for a patent to claim priority under Japanese Patent Application Nos. 2004-229498 and 2004-281226, and the entire description thereof are fully incorporated herein.

BACKGROUND ART

For diagnosis and control of diabetes, measurement of glycated proteins is extremely important. In particular, glycated albumin and hemoglobin A1c are used in many cases as indexes essential at the scene of medical treatments. The glycated albumin and hemoglobin A1c have been quantified by quantitative assays such as electrophoresis, ion-exchange chromatography, affinity chromatography, and immunization. In recent years, attempts have been made to develop an enzymatic method which enables a large-scale treatment of a large amount of a sample in a simpler manner (Non-patent Documents 1 and 2).

An example of the best known enzymatic method is a method of measuring a glycated amino acid or a glycated peptide which is generated from digestion of a glycated protein in a sample by a protease. However, a reaction of the protease is slow in general, and it was difficult for the digestion of the protein to reach 100% digestion in a short period of time even though a large amount of the protease is used. In addition, generated hydrogen peroxide can be quantified through color development of a colorant by using a peroxidase. However, the colorant, in particular, one of a leuco-type has a problem in that stability thereof is not good.

There are known methods using, as additives for promoting a reaction of the protease by denaturing a protein that is a measurement target at the time of the measurement of the glycated protein, tetrazolium salts (Non-patent Document 2 and Patent Documents 1 to 7) and sulfonic acid compounds and/or nitro compounds (Patent Documents 8 and 9). However, a tetrazolium salt strongly reacts with a reductive compound such as the glycated protein or ascorbic acid and develops color, so the tetrazolium salt causes an abnormal value in a sample containing the glycated protein in a high concentration or a sample containing ascorbic acid. In addition, many of the sulfonic acid compounds are inhibitors of an enzyme. In particular, sodium lauryl sulfate, sodium dodecylbenzenesulfonate, lithium lauryl sulfate, and the like which are often used are such strong inhibitors that they serve as reaction terminators of an enzyme which acts on the glycated amino acid and/or the glycated peptide. Further, the nitro compound is colored so that a reagent blank has an increased value, resulting in a decrease in measurement accuracy.

As described above, the "additives for promoting a reaction of the protease by denaturing a protein that is a measurement target" which are currently used are not satisfactory.

In addition, as a case where a leuco-type colorant is used in measurement, there is known measurement of hemoglobin A1c by using a reagent to which N-(carboxymethylaminocarbonyl)-4,4-bis(dimethylamino)biphenylamine (hereinafter, sometimes referred to as "DA64") (Non-patent Document 2) is added. However, there is no description regarding stability and preservation of the reagent. There has not been known a reagent containing a leuco-type colorant which has long-term stability in a liquid state.

Patent Document 1: WO 02/27012
Patent Document 2: WO 02/27330
Patent Document 3: WO 2002/027331
Patent Document 4: JP-A-2000-93199
Patent Document 5: JP-A-2001-292795
Patent Document 6: JP-A-2003-232789
Patent Document 7: WO 2000/210100
Patent Document 8: WO 2004/007760
Patent Document 9: WO 03/107011
Non-patent Document 1: Kouzuma et. al., "An enzymatic method for the measurement of glycated albumin in biological sample", Clinica Chimica Acta, 2002, 324, p. 61-71
Non-patent Document 2: Ikunosuke Sakurabayashi et. al., "New enzymatic assay for glycated hemoglobin", Clinical Chemistry, 2003, 49, 2, p. 269-274

DISCLOSURE OF THE INVENTION

Problem to be Solved by the Invention

It is an object of the present invention to provide a protease reaction promoter which is more useful than the conventionally known protease reaction promoters. In addition, another object of the present invention is to provide a stabilizer for a colorant used for detection of an enzymatic reaction.

Further, another object of the present invention is to provide a reagent which uses the protease reaction promoter and/or the stabilizer and is useful in a clinical biochemical test, in particular, measurement of hemoglobin A1c and glycated albumin, and a measurement method using the reagent.

Means for Solving the Problems

In order to achieve the above-mentioned objects, the inventors of the present invention have investigated a protease reaction promoter which does not react with a reductive substance, hardly gives influence on an enzymatic activity, and is not colored, the protease reaction promoter being other than tetrazolium salts. In addition, preservation stability of a reagent having the same composition as that disclosed in Ikunosuke Sakurabayashi et. al., Clinical Chemistry, 2003, 49, 2, p. 269-274 by using a leuco-type colorant including DA64 was investigated. As a result, it was found that the colorant significantly develops color after being preserved at 37° C. for 3 days, resulting in difficulty in measurement. Therefore, an investigation was conducted on a compound which is not known to be a stabilizer for a colorant used for the detection of the enzymatic reaction.

In addition, investigations were conducted on a reagent for measuring hemoglobin, a glycated protein, and a ratio of a glycated protein, which is characterized by using the protease reaction promoter and/or the stabilizer for a colorant, and a measurement method using the reagent. Further, investigations were conducted on a measurement reagent which is useful in a clinical biochemical test, in particular, measurement of hemoglobin A1c and glycated albumin, and a measurement method using the same.

The inventors of the present invention have focused on selection of a compound which denatures the hemoglobin or the glycated protein, changes a color tone of the hemoglobin, and promotes the reaction of the protease. As a result of an extensive investigation concerning selection of a compound which is not affected by a reductive substance, does not inhibit an enzyme activity, and does not cause a value of a blank to increase, the inventors of the present invention have found that an acetate group-containing compound, an N-acyl taurine or a salt thereof, or a polyoxyethylene alkyl ether sulfuric acid or a salt thereof has a protease reaction promoting action, and the hemoglobin, the glycated protein, or the ratio of a glycated protein can be measured in an accurate manner by using the compounds and salts.

In addition, extensive studies were made on screening of a stabilizer for a colorant used for detection of an enzymatic reaction. As a result, it was found that many of saccharides and surfactants which are generally known to be useful as stabilizers have small stabilizing effects, or inhibit color development even though they can stabilize the colorant. Among those compounds, a cyclodextrin was found to have a strong stabilizing effect on the colorant used for detection of an enzymatic reaction and not to inhibit the color developing reaction of the colorant. On the other hand, a cyclodextrin is known to maintain a compound stable by a clathrating action by which a compound is clathrated. However, it is also known that the compound is left incorporated in the cyclodextrin if once clathrated in many cases. In the present invention, there was a fear that color developing reaction does not occur when the colorant is left clathrated in the dextrin. However, it was found that a colorant, particularly a leuco-type colorant which develops color by the action of a peroxidase, is surprisingly stabilized and that the color developing reaction thereof is sufficiently maintained. Further, it was also found that: the colorant used for detection of an enzymatic reaction is made additionally stable by allowing a catalase to coexist therewith and decreasing a concentration of a buffer; and a glycated protein can accurately be measured with high sensitivity by using the method of and the reagent for stabilizing a colorant of the present invention.

Further, a reagent which uses the protease reaction promoter and/or the colorant stabilizer and is useful for a clinical biochemical test, particularly for measurement of hemoglobin A1c or glycated albumin, and a measurement method using the reagent were found, and the present invention thus has been completed.

That is, the present invention relates to the following items.

1) A protease reaction promoter, including at least one of: an acetate group-containing compound or a salt thereof; N-acyl taurine or a salt thereof; and a polyoxyethylene alkyl ether sulfuric acid or a salt thereof.

2) The protease reaction promoter according to the above item 1), in which the acetate group-containing compound or the salt thereof is an N-acyl amino acid or a salt thereof, or an alkyl ether carboxylic acid or a salt thereof.

3) The protease reaction promoter according to the above item 2), in which the N-acyl amino acid or the salt thereof is a compound represented by the following general formula (1) or a salt thereof:

$$R^1-CO-R^2 \tag{1}$$

wherein $R^1$ represents an alkyl group or an alkenyl group, and $R^2$ represents a monovalent group those are obtained by removing a hydrogen atom from an amino group in an amino acid or an amino acid derivative.

4) The protease reaction promoter according to the above item 3), in which the protease reaction promoter satisfies the following I) or II): I) $R^1$ represents $CH_3(CH_2)_n-$ (provided that, n represents an integer of 10 to 14) or a heptadec-8-enyl group; or II) the amino acid or the amino acid derivative is N-methyl alanine or sarcosine.

5) The protease reaction promoter according to the above item 2), in which the alkyl ether carboxylic acid or the salt thereof is a compound represented by the following general formula (2):

$$R^3-O-(CH_2-CH_2-O)_m-CH_2COOM \tag{2}$$

wherein $R^3$ represents an alkyl group, m represent an integer of 3 to 10, and M represents a hydrogen atom or a metal which forms a salt with carboxylic acid.

6) The protease reaction promoter according to the above item 5), in which $R^3$ is $CH_3(CH_2)_Q-$ (provided that, Q represents 10 or 11).

7) The protease reaction promoter according to any one of the above items 1) to 6), characterized in that the protease reaction promoter allows a protease reaction rate to increase by 1.5 folds or more in a method of measuring a product which is generated from a reaction of a protease, involving causing the protease to co-exist with the protease reaction promoter so that a reaction of the protease is promoted.

8) A reagent, including the protease reaction promoter according to any one of the above items 1) to 7).

9) A reagent, including the following items i) to iii): i) the protease reaction promoter according to any one of the above items 1) to 8); ii) a protease; and iii) an enzyme which acts on a glycated amino acid and/or a glycated peptide.

10) The reagent according to the above item 8) or 9), further including: a stabilizer for the protease; and/or a stabilizer for the enzyme which acts on the glycated amino acid and/or the glycated peptide.

11) The reagent according to any one of the above items 8) to 10), characterized in that the reagent is in a liquid state and is stable for 6 months or longer under refrigeration.

12) The reagent according to any one of the above items 9) to 11), in which the protease cleaves a glycated amino acid and/or a glycated peptide from a glycated N terminal of a β chain of a glycated hemoglobin or a fragment thereof without substantially cleaving a glycated amino acid and/or a glycated peptide from a glycated N terminal of an α chain of the glycated hemoglobin or a fragment thereof.

13) The reagent according to any one of the above items 9) to 12), characterized in that the enzyme which acts on the glycated amino acid and/or the glycated peptide has an action on glycated valyl-histidine higher than that on glycated valyl-leucine.

14) The reagent according to any one of the above items 8) to 13), further including: a lueco-type colorant; and a stabilizer for the colorant.

15) The reagent according to the above item 14, in which the stabilizer for the colorant is a cyclodextrin.

16) The reagent according to the above item 8) to 15), further including: a first reagent containing a protease, and an enzyme which acts on a glycated amino acid and/or a glycated peptide for eliminating a glycated amino acid and/or a glycated peptide which are/is not generated from the N terminal of the β chain of the hemoglobin; and a second reagent containing an enzyme which acts on a glycated amino acid and/or a glycated peptide for detecting the glycated amino acid and/or the glycated peptide which are/is generated from N terminal of the β chain of the hemoglobin.

17) The reagent according to any one of the above items 8) to 15), characterized in that: the first reagent contains the enzyme which acts on a glycated amino acid and/or a glycated peptide; and the second reagent contains a protease.

18) The reagent according to the above items 16) or 17), characterized in that the first reagent further contains a catalase and/or a peroxidase.

19) The reagent according to any one of the above items 8) to 18), characterized in that: the protease and the catalase are included in the same reagent and sodium azide is included in a reagent which contains no catalase in a kit composed of the first reagent and the second reagent.

20) A method of promoting a reaction of a protease, including using the protease reaction promoter according to any one of the above items 1) to 7).

21) The method of promoting a reaction of a protease according to the above item 20), characterized in that the protease reaction promoter according to the above item 7) is used to increase a protease reaction rate by 1.5 folds or more.

22) A method of measuring hemoglobin, hemoglobin A1c, or glycated albumin, including using the reagent according to any one of the above items 8) to 19).

23) The method according to the above item 22), further including sequentially performing measurement of the hemoglobin and measurement of the hemoglobin A1c in the same reaction vessel.

24) The method according to the above item 23), further including performing the measurement of the hemoglobin and the measurement of the hemoglobin A1c at the same wavelength.

25) The method according to the above item 24), further including: setting a subwavelength to obtain a value; and subtracting the value from the measurement value.

26) The method according to any one of the above items 22) to 25), further including specifically measuring the glycated amino acid and/or the glycated peptide at the N terminal of the β chain of the hemoglobin A1c.

27) The method according to any one of the above item 22) to 26), further including: measuring the hemoglobin A1c by using as a calibrator a hematolytic solution, a hemoglobin solution or a glycated peptide at the N terminal of the β chain of the hemoglobin; and calculating a quantitative value from a calibration curve.

28) The method according to the above item 22), further including sequentially performing the measurement of the albumin and the measurement of the glycated albumin in the same reaction vessel.

29) The method according to the above item 28), further including performing the measurement of the albumin and the measurement of the glycated albumin at the same wavelength.

In addition, the present invention relates to a method of calculating a hemoglobin A1c value (%), including: using, as a calibrator, any one of synthetic peptides having known concentrations selected from the group consisting of glycated valyl-histidine, glycated valyl-histidyl-leucine, glycated valyl-histidyl-leucyl-threonine, and glycated valyl-histidyl-leucyl-threonyl-proline; calculating a hemoglobin A1c concentration in a sample on the basis of a measurement value obtained by using the calibrator; and dividing the hemoglobin A1c concentration by a total hemoglobin concentration which is concomitantly or separately measured, to thereby calculate a hemoglobin A1c value (%).

In addition, another aspect of the present invention relates to a protease reaction promoter, a method of promoting a protease reaction, a reagent containing the protease reaction promoter, and a method of measuring hemoglobin, a glycated protein, or a ratio of a glycated protein which are useful for particularly quantifying hemoglobin, a glycated protein, and a ratio of a glycated protein in a blood sample by using an enzyme in an accurate, simple, and rapid manner at low cost. Specifically, the another aspect of the present invention relates to: a reagent which is obtained by adding the protease reaction promoter according to the item 1) to a reagent which is used in a method of measuring a glycated protein in a sequential manner in the same reaction vessel; and a measurement method using the same. More specifically, the measurement of the ratio of a glycated protein includes in general separate measurement of a protein and a glycated protein and conversion of the measurement values into ratios. However, the inventors of the present invention have developed a method of sequentially measuring the protein and the glycated protein in the same reaction vessel (see, JP-A-2001-204495 and the like). Combination of this method and the protease reaction promoter of the present invention enables more rapid and accurate measurement. The present invention also encompasses the combination or the like.

In addition, the present invention relates to the following items.

30) A stabilizer for a colorant used for detection of an enzymatic reaction, including a cyclodextrin.

31) The stabilizer according to the above item 30), characterized in that the cyclodextrin is a β-cyclodextrin.

32) The stabilizer according to the above item 31), characterized in that the β-cyclodextrin is methyl-β-cyclodextrin or 2-hydroxypropyl-β-cyclodextrin.

33) The stabilizer according to any one of the above items 30) to 32), characterized in that the colorant used for detection of an enzymatic reaction develops color owing to an action of a peroxidase.

34) The stabilizer according to the above item 33), characterized in that the colorant which develops color owing to the action of a peroxidase includes a leuco-type colorant.

35) A reagent, including the stabilizer according to any one of the above items 30) to 34) and the colorant used for the detection of an enzymatic reaction.

36) The reagent according to the above item 35), further including a catalase.

37) The reagent according to the above item 35) or 36), further including a buffer in a concentration of 80 mM or less at the time of measurement.

38) The reagent according to any one of the above items 35) to 37), further including a protease.

39) The reagent according to the above item 38), further including a protease reaction promoter.

40) The reagent according to any one of the above items 35) to 39), characterized in that the cyclodextrin has a concentration of 0.5 weight % or more at the time of measurement.

41) The reagent according to any one of the above items 35) to 40), characterized in that the reagent is in a liquid state and stable for 6 months or longer under refrigeration.

42) A method of stabilizing a colorant used for detection of an enzymatic reaction, including using the stabilizer according to any one of the above items 30) to 34).

43) A method of measuring a glycated protein or a ratio of a glycated protein, including using the reagent according to any one of the above items 35) to 41).

44) The method according to the above item 43), characterized in that: the glycated protein is glycated albumin, glycated hemoglobin, or hemoglobin A1c; and the ratio of a glycated protein is a glycated albumin value, a glycated hemoglobin value, or a hemoglobin A1c value.

45) Use of a cyclodextrin for stabilizing a colorant used for detection of an enzymatic reaction.

46) Use of a cyclodextrin for producing the reagent according to any one of the above items 35) to 41).

Further, the present invention relates to: a method of stabilizing a colorant used for detection of an enzymatic reaction; a reagent in which the colorant is stabilized; and a reagent for and a method of particularly quantifying a glycated protein and a ratio of a glycated protein in a blood sample in an accurate, simple, and rapid manner at low cost, which use the reagent.

Effects of the Invention

A reagent containing the protease reaction promoter of the present invention has an effect of enabling, by being added to a reagent for measuring a glycated protein or a ratio of a glycated protein, an accurate, simple, and rapid measurement thereof, and by the effect, a reagent for measurement can be provided in a large amount at low cost.

In addition, a stabilizer for the colorant used for the detection of an enzymatic reaction is provided. Thus, there can be provided: a method of stabilizing the colorant; a reagent which contains the colorant and which is excellent in preservation stability upon distribution; and a method of measuring a glycated protein and a ratio of a glycated protein by using the reagent, and a reagent for the measurement.

The reagent containing the protease reaction promoter and the stabilizer for a colorant used for detection of an enzymatic reaction of the present invention can provide a reagent for quantitatively measuring hemoglobin, hemoglobin A1c, and glycatedglycated albumin that are useful in a clinical laboratory test in an accurate, simple, and rapid manner, which is excellent in preservation stability upon distribution.

BEST MODE FOR CARRYING OUT THE INVENTION

Hereinafter, constitution and preferable embodiments of the present invention will be described in more detail.

The protease reaction promoter which can be used in the present invention may be any protease reaction promoter that promotes a protease reaction, is not affected by a reductive substance, does not inhibit an activity of an enzyme to be used concomitantly, and does not affect blank absorbance. Preferable examples of the protease reaction promoter include anionic surfactants. Among those, more preferable examples of the protease reaction promoter include an acetate-group compound or a salt thereof, N-acyl taurine or a salt thereof, and polyoxyethylene alkyl ether sulfuric acid or a salt thereof. A composition containing at least one of the protease reaction promoters which can be used in the present invention can be used as a reagent for promoting a protease reaction.

Preferable examples of the acetate group-containing compound or the salt thereof include an N-acylamino acid or a salt thereof, alkyl ether carboxylic acid or a salt thereof, a betaine acetate-type amphoteric surfactant, and imidazoline-type amphoteric surfactant. The N-acylamino acid or the salt thereof, and the alkyl ether carboxylic acid or the salt thereof are more preferable, and the N-acylamino acid or the salt thereof is particularly preferable. Further, as another aspect of the present invention, alkyl ether carboxylic acid or a salt thereof is extremely preferable in same cases. Note that the acetate group-containing compound is free from carboxylic acid, and the salt thereof may be any salt thereof with a metallic ion that forms a salt with carboxylic acid.

A preferable example of the N-acylamino acid or the salt thereof which can be used in the present invention is a compound represented by the following general formula (1) or a salt thereof:

$$R^1\text{---CO---}R^2 \qquad (1)$$

wherein $R^1$ represents an alkyl group or an alkenyl group, and $R^2$ represents a monovalent group obtained by removing a hydrogen atom from an amino group in an amino acid or an amino acid derivative.

$R^1$ represents an alkyl group or an alkenyl group. As the alkyl group represented by $R^1$, a linear or branched alkyl group having 11 to 15 carbon atoms is preferable, and a linear alkyl group having 11 to 15 carbon atoms, that is, $CH_3(CH_2)_n$— (provided that, n represents an integer of 10 to 14) is particularly preferable. Among those, a linear alkyl group having 11 carbon atoms ($CH_3(CH_2)_{10}$—; undecyl group) (or lauroyl group as represented by $CH_3(CH_2)_{10}$—CO—) is most preferable. As the alkenyl group represented by $R^1$, a linear or branched alkenyl group having 11 to 15 carbon atoms is preferable, and a linear alkenyl group having 17 or 19 carbon atoms is more preferable, with a linear alkenyl group having 17 carbon atoms being particularly preferable. The number of a double bond is preferably 2 or 1, with 1 being particularly preferable. That is, a group represented by $C_{17}H_{31}$— or $C_{17}H_{33}$— is preferable, with the group represented by $C_{17}H_{33}$— being particularly preferable. For the position of a double bond, it is preferable that a double bond be present at least at 8th position. Specific examples of the alkenyl group represented by $R^1$ include: a group obtained by removing carboxylic acid from oleic acid ($CH_3(CH_2)_7CH\text{=}CH(CH_2)_7$—; heptadec-8-enyl group); and a group obtained by removing carboxylic acid from linoleic acid ($CH_3(CH_2)_4CH\text{=}CH(CH_2)CH\text{=}CH(CH_2)_7$—; heptadeca-8,11-dienyl group).

For $R^1$, $CH_3(CH_2)_n$— (provided that, n represents an integer of 10 to 14) or a heptadec-8-enyl group, with the heptadec-8-enyl group being particularly preferable. Further, as another aspect of the present invention, $CH_3(CH_2)_n$— (provided that, n represents an integer of 10 to 14) is preferable in some cases, with $CH_3(CH_2)_{10}$— being particularly preferable.

$R^2$ represents a monovalent group obtained by removing a hydrogen atom from an amino group in an amino acid group or an amino acid derivative. A monovalent moiety of the amino group from which a hydrogen atom is removed forms a peptide bond with —CO— in the compound represented by the general formula (1). For the amino acid or the amino acid derivative, any of compounds each containing an amino group and a carboxylate group may be used, with a standard amino acid or a derivative thereof being preferable. Preferable examples of the standard amino acid include amino acids each having a nonpolar-side chain. Specifically, preferable examples thereof include glycine, alanine, valine, leucine, isoleucine, methionine, proline, phenylalanine, and tryptophan, with glycine, alanine, and valine being more preferable and glycine and alanine being most preferable.

For the derivative of the standard amino acid, an N-alkyl substitution product of a standard amino acid is preferable. Specifically, an N-methyl substitution product is preferable. In addition, for the derivative of the standard amino acid, N-methyl alanine and sarcosine are preferable, with sarcosine being particularly preferable. Further, as another aspect of the present invention, N-methyl alanine is preferable in some cases.

For the compound represented by the general formula (1), a free body thereof or a salt thereof is preferable. For the metal which forms a salt therewith, any one of metals each of which forms a salt with carboxylic acid may be used. Examples of the metal include lithium, sodium, potassium, magnesium, calcium, barium, and cesium. For the metal which forms a salt, lithium, sodium, potassium, magnesium, and calcium are preferable, with sodium and potassium being more preferable and sodium being particularly preferable. Further, as another aspect of the present invention, potassium is preferable in some cases. A free body of the compound represented by the general formula (1) is also preferable.

Specifically, preferable examples of the compound represented by the general formula (1) include sodium cocoyl sarcosinate, lauroyl sarcosine, sodium lauroyl sarcosinate, potassium lauroyl sarcosinate, sodium myristoyl sarcosinate, sodium palmitoyl sarcosinate, oleoyl sarcosine, and sodium lauroyl methyl alaninate. More preferable examples thereof include sodium cocoyl sarcosinate, sodium myristoyl sarcosinate, sodium palmitoyl sarcosinate, and sodium lauroyl methyl alaninate, and the most preferable example thereof is sodium lauroyl methyl alaninate.

The compound represented by the general formula (1) can be synthesized by a known method. For example, the compound can be obtained by reacting a long-chain fatty acid $R^1$—COOH($R^1$ has the same meaning as mentioned above) which is commercially available with an amino acid $R^2$—H ($R^2$ has the same meaning as mentioned above) which is commercially available under known conditions for peptide production. Meanwhile, the compound represented by the general formula (1) of commercially-available one such as one available from Nikko Chemicals Co., Ltd. can also be used. Those compounds each can be used after allowing the carboxylic acid to be free or subjecting to salification with a metal.

In addition, a preferable example of the alkyl ether carboxylic acid or the salt thereof include a compound represented by the general formula (2):

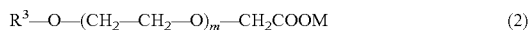

(2)

wherein $R^3$ represents an alkyl group, m represents an integer of 3 to 10, and M represents a hydrogen atom or a metal which forms a salt with carboxylic acid.

$R^3$ represents an alkyl group. For the alkyl group represented by $R^3$, a liner or branched alkyl group having 11 to 12 carbon atoms is preferable, and a linear alkyl group having 11 to 12 carbon atoms, that is, $CH_3(CH_2)_Q$— (provided that, Q represents 10 or 11) is particularly preferable.

For $R^3$, $CH_3(CH_2)_{10}$— is preferable. Further, as another aspect of the present invention, $CH_3(CH_2)_{11}$— is preferable in some cases.

m represents an integer of 3 to 10. For m, an integer of 3 to 10 is preferable, with 3, 6, and 10 being preferable, 6 and 10 being more preferable, and 6 being particularly preferable. Further, as another aspect of the present invention, an integer of 10 is preferable in some cases.

M represents a hydrogen atom or a metal which forms a salt with carboxylic acid. The metal which forms a salt may be any one of metals each of which forms a salt with carboxylic acid. Examples thereof include lithium, sodium, potassium, magnesium, calcium, barium, and cesium. For M, a hydrogen atom, lithium, sodium, potassium, magnesium, and calcium are preferable, with a hydrogen atom, sodium, and potassium being more preferable and sodium being particularly preferable. In addition, the hydrogen atom is preferable in some cases. As another aspect of the present invention, potassium is preferable in some cases.

Specifically, preferable examples of the compound represented by the general formula (2) include sodium polyoxyethylene(3)tridecyl ether acetate, sodium polyoxyethylene(6) tridecyl ether acetate, polyoxyethylene(3) tridecyl etheracetic acid, polyoxyethylene(7)tridecyl ether acetic acid, sodium polyoxyethylene(4.5)lauryl ether acetate, polyoxyethylene(4.5)lauryl ether acetic acid, sodium polyoxyethylene(10)lauryl ether acetate, and polyoxyethylene (10) lauryl ether acetic acid. Particularly preferable examples thereof include sodium polyoxyethylene(3)tridecyl ether acetate, sodium polyoxyethylene(6)tridecyl ether acetate, and polyoxyethylene(10) lauryl ether acetic acid.

The compound represented by the general formula (2) can be synthesized by a known method. For example, the compound can be obtained by reacting $R^3$—O—$(CH_2$—$CH_2$—$O)_m$-1-$CH_2$—$CH_2$—OH ($R^3$ and m have the same meanings as mentioned above) which is commercially available with a haloacetic acid derivative X—$CH_2$COOM (M has the same meaning as mentioned above, and X represents a bromine atom or a chlorine atom) which is commercially available under known conditions for ether production. Meanwhile, the compound represented by the general formula (2) of commercially-available one such as one available from Nikko Chemicals Co., Ltd. can also be used. Those compounds each can be used after allowing the carboxylic acid to be free or subjecting to salification with a metal.

Preferable examples of the N-acyl taurine or the salt thereof which can be used in the present invention include sodium N-cocoyl methyltaurinate, sodium N-lauroylmethyltaurinate, sodium N-myristoyl methyltaurinate, sodium N-palmitoyl methyltaurinate, and sodium N-stearoyl methyltaurinate. Particularly preferable examples thereof include sodium N-lauroyl methyl taurinate and sodium N-stearoyl methyl taurinate. However, any compound may be used as long as the compound is N-acyl taurine or a salt thereof, or free N-acyl taurine may be used.

The N-acyl taurine or the salt thereof which can be used in the present invention can be synthesized by a known method. For example, the N-acyl taurine or the salt thereof can be obtained by reacting commercially-available taurine with a commercially-available acylating agent. Meanwhile, the N-acyl taurine or the salt thereof of commercially-available one such as one available from Nikko Chemicals Co., Ltd. can also be used. Those N-acyl taurine or the salts thereof each can be used after allowing the carboxylic acid to be free or subjecting to salification with a metal.

In addition, preferable examples of the polyoxyethylene alkyl ether sulfuric acid or the salt thereof which can be used in the present invention include sodium polyoxyethylene(2) lauryl ether sulfate, sodium polyoxyethylene(3)lauryl ether sulfate, sodium polyoxyethylene(4)lauryl ether sulfate, triethanolamine polyoxyethylene(2)lauryl ether sulfate, triethanolamine polyoxyethylene(4)lauryl ether sulfate, sodium polyoxyethylene(3) alkyl ether sulfate, sodium polyoxyethylene(3)alkyl ether sulfate, and sodium polyoxyethylene(4) nonylphenyl ether sulfate. Particularly preferable example thereof include triethanolamine polyoxyethylene(2)lauryl ether sulfate, triethanolamine polyoxyethylene(4)lauryl ether sulfate, and triethanolamine polyoxyethylene(3)alkyl ether sulfate. However, any compound may be used as long as the compound is a polyoxyethylene alkyl ether sulfuric acid or a salt thereof, or a free polyoxyethylene alkyl ether sulfuric acid may be used.

The polyoxyethylene alkyl ether sulfuric acid or the salt thereof of commercially-available one such as one available from Nikko Chemicals Co., Ltd. can also be used.

In conclusion, specific examples of the protease reaction promoter of the present invention preferably include sodium cocoyl sarcosinate, sodium myristoyl sarcosinate, sodium palmitoyl esarcosinate, sodium lauroyl methyl alaninate, sodium polyoxyethylene(3)tridecyl ether acetate, sodium polyoxyethylene(6)tridecyl ether acetate, polyoxyethylene (10) lauryl ether acetic acid, sodium N-lauroyl methyltaurinate, sodium N-stearoyl methyltaurinate, triethanolamine polyoxyethylene(2) lauryl ether sulfate, triethanolamine polyoxyethylene(4)lauryl ether sulfate, and triethanolamine polyoxyethylene(3)alkyl ether sulfate. More preferable examples thereof include sodium lauroyl methyl alaninate, sodium polyoxyethylene(3)tridecyl ether acetate, sodium polyoxyethylene(6)tridecyl ether acetate, polyoxyethylene (10)lauryl ether acetic acid, sodium N-lauroyl methyltaurinate, sodium N-stearoyl methyltaurinate, triethanolamine polyoxyethylene(2)lauryl ether sulfate, triethanolamine polyoxyethylene(4)lauryl ether sulfate, and triethanolamine polyoxyethylene(3)alkyl ether sulfate, with sodium lauroyl methyl alaninate being most preferable.

For a usage concentration of each of the protease reaction promoters, any concentration may be used as long as the action of a protease to a protein is enhanced. For example, a lower limit of the concentration is generally 0.01% or more, preferably 0.05% or more, or most preferably 0.1% or more, and an upper limit of the concentration is 50% or less, preferably 40% or less, or most preferably 30% or less.

In addition, the protease reaction promoter of the present invention only needs to be one which increases a protease reaction rate by 1.25 folds or more. In a case where the protease reaction promoter is used in measurement of hemoglobin A1c, the protease reaction rate is preferably increased by 1.5 folds of more, more preferably by 2 folds or more, or most preferably 2.5 folds or more. In a case where the protease reaction promoter is used in measurement of glycated albumin, a rate increased by 1.5 folds or more is only required to be obtained since a protease easily acts in this case.

A degree of the protease reaction promotion may preferably be confirmed, using the method as described in Example 1, by calculating to obtain how many folds the difference in absorbance between a sample having high hemoglobin A1c value and in a sample having a low hemoglobin A1c value is larger or smaller than that in a case where no reaction promoter is added (control). Note that for the control, there may be used a test solution to which no reaction promoter is added or to which a saccharide such as sorbitol which is not confirmed to have a reaction promoting effect is added instead of the reaction promoter. In a case where screening is performed for a protease reaction promoter for albumin, the samples may be substituted by a sample having a high glycated albumin value and a sample having a low glycated albumin value.

In addition, in the present invention, examples of the substance which is generated from a reaction of a protease whose reaction is promoted by allowing at least the protease and the protease reaction promoter to coexist include a glycated amino acid, a glycated peptide, an amino acid, and a peptide. The substance is preferably a glycated amino acid or a glycated peptide. An example of the method of measuring a product generated from the protease reaction which is promoted by allowing the protease and the protease reaction promoter to coexist includes a method of measuring hemoglobin A1c and glycated albumin. However, the method may be used for methods of measuring other substances.

For the protease which can be used in the present invention, any protease can be used as long as the protease effectively acts on a glycated protein and effectively produces a glycated amino acid and/or a glycated peptide which are/is derived from the glycated protein. Preferable examples of the protease include: a proteases derived from an animal or a plant; and proteases derived from microorganisms belonging to the genus *Bacillus*, the genus *Aspergillus*, the genus *Rhizopus*, the genus *Penicillium*, the genus *Streptomyces*, the genus *Staphylococcus*, the genus *Clostridium*, the genus *Lysobacter*, or the genus *Glifila*, yeast, and microorganisms belonging to the genus *Tritirachium*, the genus *Thermus*, the genus *Pseudomonas*, or the genus *Achromobacter*. Preferable examples of the protease derived from the microorganism belonging to the genus *Bacillus* include subtilisin and metalloprotease.

In addition, in a case where the glycated protein that is a measurement target is glycated albumin, the proteases derived from the microorganisms belonging to the genera *Bacillus* and *Streptomyces* are more preferable because those proteases have larger actions on the human albumin. Particularly preferable examples of the protease include proteases derived from the genus *Bacillus* such as subtilisin and proteases type-VIII, -IX, -X, -XV, -XXIV, -XXVII, and -XXXI (those are manufactured by Sigma Aldrich Japan K.K.), Thermolysin and Nagarse (those are manufactured by Wako Pure Chemical Industries, Inc.), Olientase-90N, -10NL, -22BF, -Y, and -5BL and Nuclerisin (those are manufactured by HBI Enzymes Inc.), Proleather and Protease-N, -NL, and -S "Amano" (those are manufactured by Amano Enzymes Inc.), GODO-BNP and -BAP (those are manufactured by GODO SHUSEI CO., LTD.), Protin-A and -P, Deskin, Depireisu, Biosoak, and thermoase (those are manufactured by Daiwa Kasei K.K.), Toyozyme NEP (manufactured by Toyobo Co., Ltd.), Neutrase, Esperase, Savinase, Durazyme, Biofeed Pro, Alcalase, NUE, Pyrase, Clear Lens Pro, Everlase, Novozyme-FM, and Novolan (those are manufactured by Novozymes), Enzylon-NBS and -SA (those are manufactured by Rakuto Kasei Industrial Co., Ltd.), Alkali Protease GL440 and OptiClean-M375 plus, -L1000, and -ALP440 (those are manufactured by Kyowa Hakko Co., Ltd.), Bioprase ALP-30, Sp-4FG, XL-416F, and AL-15FG (those are manufactured by Nagase ChemteX Corporation), Aloase AP-10 and Protease YB (those are manufactured by Yakult Pharmaceutical Inc. Co., Ltd.), Corolase-N and -7089 and Veron W (those are manufactured by Higuchi Shokai Co., Ltd.), and Chirazyme P-1 (manufactured by Roche Diagnostics K.K.), with subtilisin, Nagarse, protease type-XXVII, and Chirazyme P1 being most preferable.

In addition, in a case where the glycated protein that is a measurement target is hemoglobin A1c, proteases derived from the genera *Bacillus, Aspergillus, Streptomyces, Tritirachium,* and *Lysobacter* are preferable because those proteases have larger actions on the human albumin. The proteases derived from the genera *Bacillus, Aspergillus,*

*Streptomyces*, and *Tritirachium* are more preferable. The protease derived from the genus *Lysobacter* is preferable in some aspects of the present invention. It is more preferable to use a protease derived from the genus *Bacillus* or *Lysobacter*, which cleaves a glycated amino acid and/or a glycated peptide from a glycated N terminal of a β chain of glycated hemoglobin or a fragment thereof without substantially cleaving a glycated amino acid and/or a glycated peptide from a glycated N terminal of an α chain thereof. It is most preferable to use a protease derived from *Bacillus* sp., *Bacillus thermoproteolyticus* Rokko, or *Lysobacter enzymogenes*. Note that specific examples of the protease preferably include thermolysin and thermoase (manufactured by Daiwa Kasei K.K.) derived from *Bacillus thermoproteolyticus* Rokko, Toyozyme NEP (manufactured by Toyobo Co., Ltd.), a protease derived from *Bacillus* sp. (*Bacillus* sp. ASP-842 FERM BP-08641), and a protease derived from *Lysobacter enzymogenes* (*Lysobacter enzymogenes* YK366 FERM BP-10010), with the thermolysin or the protease derived from *Lysobacter enzymogenes* being preferable and the thermolysin being particularly preferable. In addition, the protease derived from *Lysobacter enzymogenes* is particularly preferable in another aspect of the present invention.

Note that the activity of the protease which can be used in the present invention is measured by the casein-Folin method. In addition, the substrate specificity of the enzyme which cleaves a glycated amino acid and/or a glycated peptide from a glycated N terminal of a β chain of glycated hemoglobin or a fragment thereof without substantially cleaving a glycated amino acid and/or a glycated peptide from a glycated N terminal of an α chain thereof can be confirmed by using a method described in WO 2004/104203 or JP-A-2003-344052. For example, the method for confirmation described in WO 2004/104203 involves use of glycated peptides each of which is composed of 5 residues at an N terminal of an α chain and an N terminal of a β chain of hemoglobin to at least confirm a protease only produces a glycated peptide at an N terminal of the β chain, such as glycated valyl-histidine, glycated valyl-histidyl-leucine, or glycated valyl-histidyl-leucyl-threonine, without producing glycated valyl-leucine, glycated valyl-leucyl-serine, or glycated valyl-leucyl-seryl-proline. In addition, for example, the method for confirmation described in JP-A-2003-344052 involves use of glycated valyl-histidyl-paranitroanilide and glycated valyl-leucyl-paranitroanilide to confirm liberation of paranitroaniline only from the glycated valyl-histidyl-paranitroanilide.

For the enzyme which acts on a glycated amino acid and/or a glycated peptide which can be used in the present invention, any one of enzymes which effectively act on a glycated amino acid and/or a glycated peptide that are/is produced from a glycated protein by an action of the above-mentioned protease, and which can substantially measure the glycated protein may be used. Preferable examples thereof include: an enzyme which acts on a glycated amino acid and/or a glycated peptide, and which acts on an amino acid having a glycated α-amino group and/or a peptide having a glycated α-amino group in a favorable manner; and an enzyme which acts on a glycated amino acid and/or a glycated peptide, and which acts on an amino acid having a glycated ε-amino acid and/or a peptide having a glycated ε-amino acid in a favorable manner. Examples of the kind of the enzyme include dehydrogenase, oxidase, and kinase, with oxidase which is extensively investigated being preferable.

Examples of the enzyme which acts on a glycated amino acid and/or a glycated peptide, and which acts on an amino acid having a glycated ε-amino acid and/or a peptide having a glycated ε-amino acid in a favorable manner include oxidases derived from the genera *Gibberella*, *Aspergillus*, *Candida*, *Penicillium*, *Fusarium*, *Acremonium*, and *Debaryomyces*.

Further, examples of an enzyme which has a sufficient activity even in a state where the enzyme coexists with a protease and which can be produced at low cost include a gene-recombinant ketoamine oxidase (KAOD; manufactured by Asahi Kasei Pharma Corporation; described in Clinica Chimica Acta, 2002, 324, p. 61-71) and a mutant KAOD (KAOD-V; manufactured by Asahi Kasei Pharma Corporation; KAOD produced by a transformant microorganism JM109•pcm FOD5 (FERM BP-7848) which contains FOD gene as described in WO 02/27330) having significantly decreased reactivity to glycated valine. Note that the activity of the enzyme which acts on a glycated amino acid and/or a glycated peptide is measured by a method described in Clinia Chimica Acta, 2002 324, P. 61-71.

In addition, examples of the enzyme which acts on a glycated amino acid and/or a glycated peptide, and which acts on an amino acid having a glycated α-amino group and/or a peptide having a glycated α-amino group in a favorable manner include: an oxidase derived from a corynebacterium; the gene-recombinant ketoamine oxidase (KAOD; manufactured by Asahi Kasei Pharma Corporation; described in Clinica Chimica Acta, 2002, 324, p. 61-71); and enzymes which have higher effects on glycated valyl-histidine than glycated valyl-leucine and useful in the measurement of hemoglobin A1c, and which belong to the genera *Stephylium*, *Neocosmospora*, *Achaetomium*, *Chaetomium*, *Coniochaeta*, *Coniochaetidium*, *Arthrinium*, *Pyrenochaeta*, *Leptospheria*, *Pleospora*, *Ophiobolus*, *Curvularia*, and *Phoma*.

In addition, more preferable examples of the enzyme which acts on a glycated amino acid and/or a glycated peptide and which has a higher effect on glycated valyl-histidine than glycated valyl-leucine and useful in the measurement of hemoglobin A1c include enzymes derived from strains such as *Stephylium* sp. strain, *Neocosmospora vasinfecta*; IFO7590 strain, *Neocosmospora vasinfecta* 474 strain described in WO 2004/104203, *Achaetomium* sp. strain, *Chaetomium* sp., *Coniochaeta* sp. strain or *Coniochaetidium savoryi* ATCC strain, *Arthrinium* sp. TO6, *Arthrinium phaeospermum* NBRC31950, *Arthrinium phaeospermum* NBRC6620, *Arthrinium japonicum* NBRC31098, *Pyrenochaeta* sp. YH807, *Pyrenochaeta gentianicola* MAFF425531, *Pyrenochaeta terrestris* NBRC30929, *Leptospheria nodorum* (name of conidium: Phomahennebergii) NBRC7480, *Leptospheria doriolum* JCM2742, *Leptospheria maculans* (name of conidium: *Phoma lingum*) MAFF726528, *Pleospora herbarum* NBRC32012, *Pleospora betae* (name of conidium: *Phoma betae*) NBRC5918, *Ophiobolus herpotricus* NBRC6158, and *Curvulalia clavata* YH923 (FERM BP-10009). Particularly preferable example thereof include enzymes derived from *Neocosmopora vasinfecta*; IFO7590 stain, *Neocosmospora vasinfecta* 474 strain described in WO 2004/104203, and *Curvulalia clavata* YH923 (FERM BP-10009), with an enzyme derived from *Neocosmopora vasinfecta*; IFO7590 stain being most preferable. In addition, an enzyme derived from *Curvulalia clavata* YH923 (FERM BP-10009) is most preferable in another aspect of the present invention. Note that the confirmation of the substrate specificity may be performed by confirming the action of the enzyme on glycated valyl-histidine and glycated valyl-leucine as substrates.

For the stabilizer for a protease which can be used in the present invention, any one of substances that suppress a decrease in activity of a protease during preservation of a reagent may be used. In particular, the substance is preferably one that suppresses a decrease in activity of a protease when a reagent is preserved in a liquid state.

Preferable examples of the stabilizer for a protease include dimethylsulfoxide, an alcohol, calcium, sodium chloride, a tertiary ammonium salt, and a cationic surfactant of a tertiary ammonium salt. Examples of the alcohol include ethanol, propanol, ethylene glycol, and glycerin. Examples of the cationic surfactant of a tertiary ammonium salt include triethanolamine lauryl sulfate and lauryl trimethyl ammonium chloride.

In addition, for a usage concentration of each of the protease stabilizers, any concentration may be used as long as the decrease in activity of a protease is suppressed during preservation of a reagent. It is particularly preferable that the concentration be one that suppresses the decrease in activity of a protease when a reagent is preserved in a liquid state. For example, when DMSO is added as a stabilizer, a preferable concentration at which the stabilizer is added is as follows: the lower limit of the concentration is 5% or more, or preferably 10% or more; and the upper limit of the concentration is 50% or less, or preferably 40% or less.

For the stabilizer for an enzyme which acts on a glycated amino acid and/or a glycated peptide which can be used in the present invention, any one of substances that suppress at least an activity of the enzyme which acts on a glycated amino acid and/or a glycated peptide during the preservation of a reagent may be used. In particular, it is preferable to use a substance that suppresses at least a decrease in activity of an enzyme which acts on a glycated amino acid and/or a glycated peptide when a reagent is preserved in a liquid state.

Preferable examples of the stabilizer for an enzyme which acts on a glycated amino acid and/or a glycated peptide include sugar alcohols, sucrose, magnesium, calcium, ammonium sulfate, amino acids, and sarcosine. Examples of the sugar alcohols include sorbitol, mannitol, trehalose, and glycerin. In addition, all of the amino acids have strong stabilizing effects. Standard amino acids are particularly preferable, and among those, proline, glutamic acid, alanine, valine, glycine, and lysine are more preferable.

In addition, for the usage concentration of the stabilizer for the enzymes which act on a glycated amino acid and/or a glycated peptide, any concentration may be used as long as a decrease in activity of the enzyme which acts on a glycated amino acid and/or glycated peptide is suppressed during the preservation of a reagent. It is particularly preferable that the concentration be one that suppresses a decrease in activity of an enzyme which acts on a glycated amino acid and/or a glycated peptide when a reagent is preserved in a liquid state. For example, when sorbitol is added as a stabilizer, a preferable concentration at which the stabilizer is added is as follows: the lower limit of the concentration is 0.1% or more, or preferably 0.2% or more; and the upper limit of the concentration is 30% or less, or preferably 20% or less.

The stability of the reagent of the present invention can be determined, for example, as described hereinbelow. A reagent in a liquid state is preserved under refrigeration (2 to 10° C.) at a temperature of preferably 4° C. for 6 months. Alternatively, the preservation may be performed under conditions of 37° C. and 4 days. The reagent after the preservation and a reagent before the preservation are used in measurement of concentrations of plasma or hemolytic solution (blood which is subjected to hemolytic treatment) as samples by using, as a calibrator, glycated albumin or hemoglobin A1c (or glycated hemoglobin) having a known concentration, and the concentrations were compared between the reagent before the preservation and the reagent after the preservation. It is preferable that the difference between the concentrations be small, and it is extremely preferable that there is no difference between the concentrations.

The method of promoting a protease reaction by using the protease reaction promoter of the present invention is extremely useful.

Examples of the colorant used for detection of an enzymatic reaction which can be used in the present invention include co-enzymes, tetrazolium salts, Trinder's reagents, and leuco-type reagents. Co-enzymes, Trinder's reagents, and leuco-type reagents are preferable. Colorants that develop color by the action of peroxidase, such as Trinder's reagents and leuco-type reagents are more preferable, and a leuco-type reagent is particularly preferable.

For example, in a case where a glycated amino acid and/or a glycated peptide are/is measured by using a dehydrogenase, there can be used: a co-enzyme such as NAD (Nicotinamide adenine dinucleotide); or any one of various tetrazolium salts typified by nitroblue tetrazolium, tetrazolium blue, 2-(4-iodophenyl)-3-(4-nitrophenyl)-5-(2,4-disulfophenyl)-2H-tetrazolium: WST-1,2-(4-iodophenyl)-3-(2,4-dinitrophenyl)-5-(2,4-disulfophenyl)-2H-tetrazolium: WST-3,2-(2-methoxy-4-nitrophenyl)-3-(4-nitrophenyl)-5-(2,4-disulfophenyl)-2H-tetrazolium: WSR-8 (those are manufactured by Dojindo Laboratories).

In addition, in a case where a glycated amino acid and/or a glycated peptide are/is measured by using an oxidase, there can be used a Trinder's reagent or a leuco-type reagent that generates a colorant through oxidation condensation of hydrogen peroxide which is generated by an action of the oxidase with a coupler such as 4-aminoantipyrine (4-AA) or 3-methyl-2-benzothiazolinone hydrazone (MBTH) and with a chromogen such as phenol under the presence of peroxidase.

For a hydrogen donor of a Trinder-type reagent, there can be used a phenol derivative, an aniline derivative, toluidine derivative, and the like. Specific examples thereof include sodium N-(3-sulfopropyl)aniline monohydride (HALPS), sodium N-ethyl-N-(3-sulfopropyl)-3-methylaniline monohydride (TOPS), sodium N-ethyl-N-(2-hydroxy-3-sulfopropyl)-3,5-dimethoxyaniline monohydride (MAOS), sodium N-(3-sulfpropyl)-3,5-dimethoxyaniline monohydride (HDAPS), sodium N-(2-hydroxy-3-sulfopropyl)-3,5-dimethoxyaniline (HDAOS), sodium N-ethyl-N-(3-sulfopropyl)-3,5-dimethoxyaniline monohydride (DAPS), sodium N-ethyl-N-(2-hydroxy-3-sulfopropyl)-3,5-dimethoxyaniline (DAOS), sodium N-ethyl-N-(3-sulfopropyl)aniline (ALPS), sodium N-ethyl-N-(3-sulfopropyl)-3-methoxyaniline monohydride (ADPS), sodium N-ethyl-N-(2-hydroxy-3-sulfopropyl)-3-methoxyaniline dihydride (ADOS), N-ethyl-N-(2-hydroxy-3-sulfopropyl)-m-toluidine (TOOS), and disodium N,N-bis(4-sulfobutyl)-3-methylaniline (TODB) (those are manufactured by Dojindo Laboratories).

For the leuco-type colorant which can be used in the present invention, any colorant may be used. Examples thereof include colorants which are easily available, such as: N-(carboxymethylaminocarbonyl)-4,4-bis(dimethylamino) biphenyl amine (DA64) and 10-(carboxymethylaminocarbonyl)-3,7-bis(dimethylamino)phenothiazine (DA67) (those are manufactured by Wako Pure Chemical Industries, Inc. and the like); 2,2'-azinobis(3-ethylbenzthiazoline-6-sulfonate (ABTS), bis-(4-diethylaminophenyl)-2-sulfophenylmethane (BSPM), bis[3-bis(4-chlorophenyl)methyl-4-dimethylaminophenyl]amine (BCMA), and 10-N-methylcarbamoyl-3,7-dimethylamino-10H-phenothiazine (MCDP) (those are manufactured by Wako Pure Chemical Industries, Inc.); o-tolidine, 3,3'-diaminobenzidine.4HCl (DAB), 3-(4-hydroxyphenyl)propionic acid (HPPA), N,N'-bis(2-hydroxy-3-sulfophenyl)tolidine.2Na.4H$_2$O (SAT-3), 3,3',5,5'-tetramethylbenzidine (TMBZ), N-(3-sulfopropyl)-3,3',5,5'-tetramethylbenzidine.Na (TMBZ-PS), and N,N',N'',N''-hexa(3-sulfpropyl)-4,4',4''-triaminotriphenylm ethane.6Na (TPM-PS) (those are manufactured by Dojindo Laboratories).

For the stabilizer for the colorant which can be used in the present invention, any one of substances may be used as long as it increases stability of the colorant. A preferable example thereof is a cyclodextrin. Any cyclodextrin may be used as long as a stabilizing effect on the colorant used for the detection of an enzymatic reaction is attained. Examples of the cyclodextrin include α-cyclodextrins, β-cyclodextrins, and γ-cyclodextrins, with β-cyclodextrins and γ-cyclodextrins being preferable and β-cyclodextrins being particularly preferable. Examples of the α-cyclodextrins include α-cyclodextrin. Examples of the γ-cyclodextrins include γ-cyclodextrin and carboxymethyl-γ-cyclodextrin, with γ-cyclodextrin being preferable. The carboxymethyl-γ-cyclodextrin is preferable in some cases. Examples of the β-cyclodextrins include β-cyclodextrin, carboxymethyl-β-cyclodextrin, dimethyl-β-cyclodextrin, monoamino-β-cyclodextrin, 2-hydroxypropyl-β-cyclodextrin, and methyl-β-cyclodextrin, with 2-hydroxypropyl-β-cyclodextrin and methyl-β-cyclodextrin being preferable and 2-hydroxypropyl-β-cyclodextrin being particularly preferable. In addition, methyl-β-cyclodextrin is extremely preferable in some cases.

In conclusion, preferable examples of the cyclodextrin include: α-cyclodextrin, β-cyclodextrin, γ-cyclodextrin, carboxymethyl-γ-cyclodextrin, carboxymethyl-β-cyclodextrin, dimethyl-β-cyclodextrin, and monoamino-β-cyclodextrin (those are available from Sigma Aldrich Japan K.K. and the like); and 2-hydroxypropyl-β-cyclodextrin and methyl-β-cyclodextrin (those are available from Nihon Shokuhin Kako Co., Ltd. and the like). 2-hydroxypropyl-β-cyclodextrin and methyl-β-cyclodextrin are more preferable, and 2-hydroxypropyl-β-cyclodextrin is particularly preferable. In addition, methyl-β-cyclodextrin is extremely preferable in some cases.

The cyclodextrin can be used as a stabilizer for a colorant used for the detection of an enzymatic reaction. In addition, the cyclodextrin can be used for stabilizing a colorant used for the detection of an enzymatic reaction. Further, the cyclodextrin can be used for producing a reagent for stabilizing a colorant used for the detection of an enzymatic reaction.

For the usage concentration of the colorant used for the detection of an enzymatic reaction, any concentration may be used as long as color development is sufficiently maintained during preservation of a reagent. It is particularly preferable that the concentration be one that maintains sufficient color development when a reagent is preserved in a liquid state. For example, when DA67 is used, a preferable concentration is as follows: the lower limit of the concentration is 1 μM or more, or preferably 2 μM or more; and the upper limit of the concentration is 100 mM or less, or preferably 50 mM or less.

For the usage concentration of the cyclodextrin, any concentration may be used as long as deterioration of the colorant used for detection of an enzymatic reaction is suppressed during preservation of a reagent. It is particularly preferable that the concentration be one that suppresses deterioration of a colorant when a reagent is preserved in a liquid state. For example, when methyl-β-cyclodextrin is added as a stabilizer, a preferable concentration is as follows: the lower limit of the concentration is 0.5% or more, or preferably 1.0% or more; and the upper limit of the concentration is 50% or less, or preferably 40% or less. In addition, a preferable proportion between a colorant and a cyclodextrin in weight ratio is as follows: the lower limit of the proportion colorant:cyclodextrin is 1:0.01 or more, or preferably 1:0.04 or more; and the upper limit of the proportion colorant:cyclodextrin is 1:5,000,000 or less, or preferably 1:3,300,000 or less.

Specific examples of a preferable buffer which can be used in the present invention preferably include Good' buffers such as buffers using 3-[4-(2-hydroxyethyl)-1-piperazinyl]propanesulfonic acid (EPPS), 2-[4-(2-hydroxyethyl)-1-piperazinyl]ethanesulfonic acid (HEPES), 2-hydroxy-3-[4-(2-hydroxyethyl)-1-piperazinyl]propanesulfonic acid (HEPPSO), N-(2-acetamide)-2-aminoethanesulfonic acid (ACES), N-(2-acetamide)iminodiacetic acid (ADA), N,N-bis (2-hydroxyethyl)-2-aminoethanesulfonic acid (BES), N,N-bis(2-hydroxyethyl)glycine (Bicine), bis(2-hydroxyethyl) iminotris(hydroxymethyl)methane (Bis-Tris), N-cyclohexyl-3-aminopropanesulfonic acid (CAPS), N-cyclohexyl-2-hydroxy-3-aminopropanesulfonic acid (CAPSO), N-cyclohexyl-2-aminoethanesulfonic acid (CHES), 3-[N,N-bis(2-hydroxyethyl)amino]-2-hydroxypropanesulfonic acid (DIPSO), 2-morphilinoethanesulfonic acid (MES), 3-morphilinopropanesulfonic acid (MOPS), 2-hydroxy-3-morphilinopropanesulfonic acid (MOPSO), piperazine-1,4-bis (2-ethanesulfonic acid) (PIPES), piperazine-1,4-bis(2-hydroxy-3-propanesulfonic acid) (POPSO), N-tris (hydroxymethyl)methyl-3-aminopropanesulfonic acid (TAPS), 2-hydroxy-N-tris(hydroxymethyl)methyl-3-aminopropanesulfonic acid (TAPSO), N-tris(hydroxymethyl)methyl-2-aminopropanesulfonic acid (TES), N-[tris(hydroxymethyl)methyl]glycine (Tricine), and trishydroxymethylaminomethane (Tris), and the like; and boric acid, ammonia, glycine, carbonic acid, acetic acid, phosphoric acid, diethanolamine, p-phenolsulfonic acid, 2-amino-2-methylpropane-1,3-diol, cacodylic acid, citric acid, maleic acid, veronal, and 3,3-dimethylglutaric acid.

More preferable examples of the buffer include buffers each having a buffering action at around neutral pH, such as EPPS, HEPES, HEPPSO, ACES, ADA, BES, Bicine, Bis-Tris, CHES, DIPSO, MES, MOPS, MOPSO, PIPES, POPSO, TAPS, TAPSO, TES, Tricine, Tris, ACES, ADA, boric acid, ammonia, glycine, phosphoric acid, diethanolamine, p-phenolsulfonic acid, 2-amino-2-methylpropane-1,3-diol, cacodylic acid, citric acid, maleic acid, veronal, and 3,3-dimethylglutaric acid, with 3,3-dimethylglutaric acid being most preferable.

The reagent containing the colorant used for detection of an enzymatic reaction of the present invention in a stabilized state is not particularly limited as long as the reagent is one at least containing the stabilizer for the colorant used for detection of an enzymatic reaction of the present invention and the colorant used for detection of an enzymatic reaction.

In addition, it is extremely preferable to allow a catalase to coexist in the reagent of the present invention. The coexistence of the catalase is caused for the purpose of eliminating hydrogen peroxide generated during preservation to suppress color development of a colorant as much as possible during the preservation. For the catalase which can be used in the present invention, any one of enzymes each having a catalase activity may be used. Examples thereof include an enzyme derived from *Aspergillus niger* and an enzyme derived from a bovine liver, with an enzyme derived from *Aspergillus niger* being particularly preferable. In addition, the enzyme derived from a bovine liver is particularly preferable in some cases. Note that the enzyme derived from *Aspergillus niger* and the enzyme derived from a bovine liver are available from Sigma Aldrich Japan K.K. and the like.

For the reagent for and the method of measuring hemoglobin which can be used in the present invention, any one of reagents and measurement methods may be used as long as they are a reagent for and a method of measuring hemoglobin by using the protease reaction promoter of the present invention. Preferable examples thereof include a reagent containing the compound containing the acetate group or the salt thereof, N-acyl taurine or the salt thereof, or polyoxyethylene alkyl ether sulfuric acid or the salt thereof, and a measurement method using the reagent. In particular, a reagent containing, as the compound containing the acetate group or the salt thereof, the N-acylamino acid or the salt thereof or the alkyl ether carboxylic acid or the salt thereof, and a measurement method using the reagent are particularly preferable. The usage concentration of each of the protease reaction promoters may be any one as long as hemoglobin can be measured. For example, in general, the lower limit of the concentration is 0.01% or more, preferably 0.05% or more, or most preferably 0.1% or more, and the upper limit of the concentration is 50% or less, more preferably 40% or less, or most preferably 30% or less.

The operation of the hemoglobin measurement which can be used in the present invention may be performed in such a manner that: the above-mentioned reagent for hemoglobin quantification is added with 0.001 to 0.5 ml of an analyte solution to allow a reaction at a temperature of 37° C.; and color tone (absorbance) of hemoglobin is measured after a predetermined period of time has passed after the initiation of the reaction. For the color tone of hemoglobin, absorbance may be measured at 200 nm to 1,000 nm, or preferably 280 nm to 800 nm. In this case, an amount of hemoglobin in the analyte solution can be determined by comparing a change in absorbance of the analyte measured with that of a sample containing a predetermined concentration of hemoglobin.

For the reagent for measuring a glycated protein which can be used in the present invention, any reagent may be used as long as the reagent is used for measuring a glycated protein with use of the protease reaction promoter of the present invention and/or the stabilizer of the colorant used for detection of an enzymatic reaction which is typified by a cyclodextrin of the present invention. Preferable examples thereof include reagents each containing the above-mentioned protease and an enzyme which acts on a glycated amino acid and/or a glycated peptide. The protease and the enzyme which acts on a glycated amino acid and/or a glycated peptide can be formulated in the same solution. However, it is preferable to use a reagent composed of a protease reagent containing a protease and an analyte reagent containing an enzyme which acts on a glycated amino acid and/or a glycated peptide. The protease reaction promoter may be formulated in either of the protease reagent and the analyte reagent. The protease reaction promoter may exist at the time when the protease acts on a glycated protein or in advance. In addition, it is more preferable that the reagent containing a protease contain a protease stabilizer and that the reagent containing an enzyme which acts on a glycated amino acid and/or a glycated peptide contain a stabilizer for the enzyme which acts on a glycated amino acid and/or a glycated peptide.

Note that it is more preferable that a colorant used for detection of an enzymatic reaction, a stabilizer for the colorant used for detection of an enzymatic reaction which is typified by a cyclodextrin, and a catalase coexist and peroxidase be added in another reagent so that they are mixed at the time of measurement. This is because the coexistence of the colorant and the peroxidase may promotes a reaction during preservation, resulting in color development.

Specifically, pH, a buffer, and a protease concentration for the protease reagent which can be used in the present invention are determined so that the proteolytic reaction efficiently proceeds, and then a protease reaction promoter and protease stabilizer are appropriately prepared and added to the protease reagent in effective concentrations.

The buffer which can be used in the present invention may be any buffer as long as the stability of the colorant used for detection of an enzymatic reaction is not affected. Specific examples thereof are as described above. It is important to set a usage concentration of the buffer to a buffer concentration at the time of measurement. The buffer concentration at the time of measurement may be such that: the upper limit thereof is 80 mM or less, or more preferably 50 mM or less; and the lower limit thereof is 0.1 mM or more, or preferably 1 mM or more.

For example, in a case of using the protease type-XXIV (manufactured by Sigma Aldrich Japan K.K.) when the protein is albumin and a measurement target is glycated albumin, the pH of the reaction is preferably selected from 7 to 10 because of a strong proteolytic activity at a pH of around 7 to 10.

In addition, in a case of using the above-mentioned Toyozyme NEP (manufactured by Toyobo Co., Ltd.) when the protein is hemoglobin and a measurement target is glycated hemoglobin or hemoglobin A1c, the pH of the reaction is preferably selected from 6.0 to 9.0 because of a strong proteolytic activity at a pH around 6.0 to 9.0.

The protease concentration only needs to be one at which the protein in an analyte solution can sufficiently be decomposed in a reaction time which is actually used. The lower limit thereof is 10 U/ml or more, preferably 100 U/ml or more, or most preferably 500 U/ml or more, and the upper limit thereof is $1.0 \times 10^6$ U/ml or less, preferably $5.0 \times 10^5$ U/ml or less, or most preferably $3.0 \times 10^5$ U/ml or less.

Any protease reaction promoter may be used as long as it is the protease reaction promoter of the present invention. The usage concentration thereof may be any one at which a protein is effectively denatured and an action of a protease on a protein is enhanced. For example, in general, the lower limit thereof is 0.01% or more, preferably 0.05% or more, or most preferably 0.1% or more, and the upper limit thereof is 50% or less, preferably 40% or less, or most preferably 30% or less.

For the usage concentration of the protease stabilizer, any concentration can be used as long as a stable reagent property is exhibited even when the reagent is preserved in a liquid state for 6 months under refrigeration. For example, when dimethylsulfoxide is used, in general, the lower limit of the concentration is 1% or more, or preferably 5% or more, and the upper limit of the concentration is 60% or less, or preferably 50% or less.

For the usage concentration of the catalase, any concentration may be used as long as the catalase can eliminate hydrogen peroxide or the like which makes the colorant used for the detection of an enzymatic reaction unstable. For example, in general, the lower limit of the concentration is 0.1 U/ml or more, preferably 1 U/ml or more, and most preferably 2 U/ml or more, and the upper limit of the concentration is 3,000 U/ml or less, preferably 1,500 U/ml or less.

The composition of the measurement reagent containing the enzyme which acts on a glycated amino acid and/or a glycated peptide which can be used in the present invention may be determined in such a manner that: the pH of the measurement reagent is selected so that a reaction efficiently proceeds with regard to the optimal pH of the enzyme which acts on the glycated amino acid and/or the glycated peptide to be used; and the amount of the enzyme which acts on the glycated amino acid and/or the glycated peptide is determined. Next, when a peroxidase, a stabilizer for the enzyme which acts on the glycated amino acid and/or the glycated peptide, and a catalase in a protease reagent are used, an azide such as sodium azide which stops the actions thereof may be added.

For example, in a case where the KAOD or the KAOD-V (manufactured by Asahi Kasei Pharma Corporation) is used when the protein is albumin and the measurement target is glycated albumin, the pH of the reaction is preferably selected from 6.5 to 10 because 50% or more of the maximum activity is exhibited in a wide region of pH 6.5 to 10. In addition, for example, in a case where the KAOD derived from *Curvularia clavata* YH923 is used when the protein is hemoglobin and the measurement target is glycated hemoglobin or hemoglobin A1c, the pH of the reaction is preferably selected from 6.0 to 10 because 50% or more of the maximum activity is exhibited in a wide region of pH 6.0 to 10.

For the usage concentration of the enzyme which acts on a glycated amino acid and/or a glycated peptide, any concentration may be used as long as the glycated protein can be measured. In general, the lower limit of the concentration is 0.5 U/ml or more, or preferably 1 U/ml or more, and the upper limit of the concentration is 1,000 U/ml or less, or preferably 500 U/ml or less.

For the usage concentration of the peroxidase, any concentration may be used as long as hydrogen peroxide generated from a measurement system can be measured. In general, the lower limit of the concentration is 0.01 U/ml or more, or preferably 0.1 U/ml or more, and the upper limit of the concentration is 100 U/ml or less, or preferably 50 U/ml or less.

For the usage concentration of the stabilizer for the enzyme which acts on a glycated amino acid and/or a glycated peptide, any concentration may be used as long as a stable reagent property is exhibited when the reagent is preserved in a liquid state for 6 months under refrigeration. For example, in a case where sorbitol is used, in general, the lower limit of the concentration is 0.1% or more, or preferably 1% or more, and the upper limit of the concentration is 30% or less, or preferably 20% or less.

The azide in a case where the azide is used to stop the catalase reaction may be used in any concentration as long as the catalase activity is sufficiently stopped. For example, sodium azide is generally used in a usage concentration of the lower limit of 0.01% or more, or preferably 0.05% or more and the upper limit of 10% or less, or preferably 5% or less.

When the enzyme which acts on a glycated amino acid and/or a glycated peptide is used in the method of measuring a glycated protein according to the present invention, the detection of the action of the enzyme may be performed when, for example, a dehydrogenase is used as the enzyme, by measuring an amount of change of a co-enzyme as the following. For example, when NAD is used as the co-enzyme, the amount of change due to the co-enzyme is directly quantified by a known technique such as a technique which involves measuring reduced NAD that is a reduced co-enzyme at a wavelength around 340 nm that is the maximum absorbance wavelength region of the reduced NAD. Alternatively, the generated reduced co-enzyme may be indirectly quantified by using a reducing coloring reagent such as any one of various diafolase, electron carriers such as phenadinemetosulfate, and various tetrazolium salts which are typified by nitrotetrazolium, 2-(4-lodophenyl)-3-(4-nitrophenyl)-5-(2,4-disulfophenyl)-2H-tetrazolium, monosodium salt (WST-1), and 2-(4-lodophenyl)-3-(2,4-dinitrophenyl)-5-(2,4-disulfophenyl)-2H-tetrazolium, monosodium salt (WST-3) (those are manufactured by Dojindo Laboratories). Alternatively, the amount of change may be directly or indirectly measured by any of other known methods.

In addition, when, for example, an oxidase is used, it is preferable to measure a consumption amount of the enzyme or the amount of a reaction product. When, for example, ketoamine oxidase is used, hydrogen peroxide and glucosone are produced as reaction products from the reaction, and the hydrogen peroxide and glucosone can be directly or indirectly measured by any of known methods.

The amount of the hydrogen peroxide may be quantified as the following. For example, a colorant or the like produced by using a peroxidase may be quantified by means of color development, luminescence, fluorescence, or the like, or by an electrochemical procedure. Alternatively, the amount of aldehyde which is produced from an alcohol by using a catalase or the like may be quantified.

Examples of a color development system for the hydrogen peroxide which can be used include: a Trinder's reagent which produces a colorant through oxidation condensation of a coupler such as 4-aminoantipyrine (4-AA) or 3-methyl-2-benzothiazolinone hydrazone (MBTH) and a chromogen such as phenol under the presence of a peroxidase; and a lueco-type reagent which directly oxidases and develops color under the presence of a peroxidase, such as N-(carboxymethylaminocarbonyl)-4,4-bis(dimethylamino)biphenyla mine (DA64) or 1-(carboxymethylaminocarbonyl)-3,7-bis(dimethylamino)phenothiazine (DA67) (those are manufactured by Wako Pure Chemical Industries, Inc.).

In addition, when hydrogen peroxide is measured by using an electrode, the material of the electrode is not particularly limited as long as the material can give and receive electrons to and from the hydrogen peroxide. Examples of the material include platinum, gold, and silver. For a measurement method using an electrode, any one of known methods such as amperometry, potentiometry, and coulometry can be used. Further, an electron transferring substance may intervene between an oxidase or a substrate and an electrode so that obtained oxidation-reduction electrical current or an electrical quantity thereof may be measured. For the electron transferring substance, any substance having an electron transferring function such as a ferrocene derivative or a quinone derivative can be used. In addition, an electron transferring substance may intervene between the hydrogen peroxide which is generated from an oxidase reaction and an electrode so that obtained oxidation-reduction electrical current or an electrical quantity thereof may be measured.

Further, it is needless to say that the protease is used alone in the measurement method and the measurement reagent of the present invention. In addition, other endoprotease or other exoprotease may be allowed to function before or after the reaction of the protease or at the same time as the reaction of the protease.

In addition, surfactants, salts, antiseptics, and the like may be appropriately selected and added to the composition of an enzymatic reaction reagent for measuring a glycated protein of the present invention.

Examples of the additive which may be appropriately added include: 0.01 to 10%, or preferably 0.05 to 5% of a surfactant such as polyoxyethylene alkyl ethers, polyoxyethylene sorbitan fatty acid esters, or polyvinyl alcohol; 1 mM to 5 M, or preferably 10 mM to 1 M of various metallic salts such as lithium chloride, sodium chloride, potassium chloride, manganese chloride, cobalt chloride, zinc chloride, and calcium chloride; and 1 to 10%, or preferably 0.05 to 1% of various antiseptics such as sodium azide. As one of the various antiseptics, 0.01 to 10%, or preferably 0.02 to 5% of proclin (manufactured by SUPELCO) may appropriately be added.

The method of measuring a glycated protein which can be used in the present invention may involve: adding 0.001 to 0.5 ml of an analyte solution to the enzymatic reaction reagent for measuring a glycated protein of the present invention to allow a reaction to proceed at a temperature of 37° C.; and when a rate assay is performed, directly or indirectly measuring the amount of change of a co-enzyme, dissolved oxygen, hydrogen peroxide, or other product which is obtained between 2 time points after a certain period of time of the initiation of the reaction, for several minutes to several tens of minutes, such as 1 minute from 3 minutes to 4 minutes after the initiation, or 5 minutes from 3 minutes to 8 minutes after the initiation, or when an end point assay is performed, measuring the amount of change of a co-enzyme, dissolved oxygen, hydrogen peroxide, or other product after a certain period of time of the initiation of the detection reaction in the same manner. In this case, when the results thereof are compared with the change in absorbance or the like obtained from measurement using a glycated protein having a predetermined concentration, the amount of the glycated protein in the analyte solution can be determined.

Examples of the calibrator which can be used in the measurement method of the present invention may include, in addition to the protein having a predetermined concentration, a glycated amino acid or a glycated peptide having a predetermined concentration. Examples of the glycated amino acid or the glycated peptide which may be used include commercially-available synthetic peptides. In a case of measuring hemoglobin A1c, there can be used glycated valyl-histidine, glycated valyl-histidyl-leucine, glycated valyl-histidyl-leucyl-threonine, glycated valyl-histidyl-leucyl-threonyl-proline, or the like. The peptide concentration in a calibrator may be one enough for allowing measurement of the concentration of the peptide generated from a sample.

The composition of the reagent for measuring a ratio of a glycated protein which can be used in the present invention may be prepared such that the composition of the reagent for measuring a glycated protein is separately or concomitantly added with a composition for measuring a protein. For example, when the protein is glycated albumin, albumin is separately measured. When the protein is glycated hemoglobin or hemoglobin A1c, hemoglobin is separately measured. The measurement of albumin or hemoglobin may be performed by using any one of known methods.

Any method may be used for the composition for separately measuring albumin as long as the method is a known method for measuring albumin. Examples of the method include methods each of which uses an albumin-specific colorant such as bromcresol green (hereinafter, abbreviated as BCG), bromcresol purple (hereinafter, abbreviated as BCP), bromophenol blue (hereinafter, abbreviated as BPB), methyl orange (hereinafter, abbreviated as MO), or 2-(4-hydroxybenzeneazo)benzoic acid (hereinafter, abbreviated as HABA). Further, when the target protein is hemoglobin, any method may be used as long as the method is a known method for measuring hemoglobin. Examples of the method include a methemoglobin method, a cyanmethemoglobin method, an azidemethemoglobin method, a green chromophore formation method, and an oxyhemoglobin method. The green chromophore formation method is a method which involves allowing a green chromophore formation reagent to react with hemoglobin to form a stable product (green chromophore). The green chromophore has an absorption spectrum similar to that of alkaline hematin D-575 as described in UK Patent No. 2052056.

For the method of sequentially performing measurement of hemoglobin and measurement of hemoglobin A1c in the same reaction vessel which can be used in the present invention, any method may be used as long as the method involves use of the reagent containing the protease reaction promoter of the present invention. Specifically, the method involves: adding a sample to a first reaction reagent containing the protease reaction promoter; measuring absorbance at a wavelength specific to hemoglobin, such as 220 nm to 900 nm, or preferably 280 nm to 800 nm after a certain period of time such as after 3 minutes or 5 minutes; adding a second reagent containing ketoamine oxidase to the mixture; and measuring absorbance near the maximum absorption of a colorant which develops color after a certain period of time such as after 3 minutes or 5 minutes. In this case, the protease may be included in either of the first reaction reagent and the second reaction reagent. In addition, the results are compared with the absorbance of a sample having a predetermined hemoglobin concentration and a predetermined hemoglobin A1c concentration, whereby the absorbance can be converted into the hemoglobin concentration and hemoglobin A1c concentration. In general, a hemoglobin A1c value is represented by a ratio of a hemoglobin A1c concentration to a total hemoglobin concentration, so the hemoglobin A1c concentration may be converted into a ratio by dividing the hemoglobin A1c concentration by the total hemoglobin concentration.

Further, the method characterized by including sequentially performing measurement of hemoglobin and measurement of hemoglobin A1c in the same vessel of the present invention preferably includes: measuring hemoglobin and hemoglobin A1c at the same wavelength; measuring the hemoglobin and hemoglobin A1c at a subwavelength for separately deducting an influence such as cloud due to the samples; and subtracting absorbance at the subwavelength from the absorbance at the measurement wavelength. Any wavelength may be used as the measurement wavelength. However, a wavelength near the maximum absorption of a colorant which develops color is preferable. For example, when the DA67 is used, measurement can be performed at 500 nm to 700 nm, or preferably 550 nm to 660 nm, and at a subwavelength of 600 nm to 800 nm, or preferably 650 nm to 750 nm.

The reagent of the present invention can be provided in a form of a liquid product, a frozen product of the liquid product, a freeze-dry product of the liquid product, or a dry product of the liquid product (which is obtained by heat drying and/or air drying and/or drying under reduced pressure or the like). A preferable reagent form is a liquid product.

For the sample to be a measurement target of the present invention, there may be used any one of analyte solutions each at least containing hemoglobin or glycated protein. Preferable examples of the analyte solution include blood components such as serum, plasma, blood cells, whole blood, and separated red blood cells. In addition, protease treatment solution (hemolytic solution) obtained by fragmenting the separated red blood cells or glycated hemoglobin by protease in advance may be used as preferable analyte solutions. Note that the separation of the red blood cells can be performed by a known centrifugation method involving, for example, separation at 3,000 rpm for about 3 minutes. In addition, as a method for hemolysis for the separated red blood cell, the separated red blood cell only needs to be subjected to hemolysis with distilled water.

Examples of the glycated protein to be the measurement target of the reagent for and the method of measuring a glycated protein of the present invention include glycated albumin and hemoglobin A1c (glycated hemoglobin may be included). However, the glycated protein to be the measurement target is not limited thereto, and any one of glycated proteins may be measured.

In a case where measurement is affected because a sample originally contains a glycated amino acid and/or a glycated peptide in addition to the glycated protein that is a measurement target such as hemoglobin A1c or glycated albumin, for example, in a case where a sample taken from a patient who receives infusion of high-calorie amino acids is measured or a case where hemoglobin A1c is measured, if glycation of an N terminal of a β chain of interest can not be specifically measured by means of only the specificity of the enzyme because of the presence of a large amount of glycated amino acids in a molecule, it should be required to eliminate those components other than the component of interest before the measurement.

An elimination reaction may be performed by using an enzyme which acts on a glycated amino acid and/or a glycated peptide. For example, in the case where the measurement is affected because the glycated amino acid and/or the glycated peptide are/is originally included, there may be used a reagent containing: a first reagent containing the enzyme which acts on the glycated amino acid and/or the glycated peptide; and a second reagent containing a protease.

The reagent containing a first reagent containing the enzyme which acts on the glycated amino acid and/or the glycated peptide, and a second reagent containing a protease can be formulated using the protease reagent and the reagent for glycated amino measurement which do not contain reagent not including the elimination reaction. When a mixing ratio between the first reagent and the second reagent not 1:1, for example, when the mixing ratio is 1:3, 1:4, 1:5, or the like, the formulation may appropriately be adjusted so that concentrations of respective components effectively function at the time of mixing. In other words, when the mixing ratio between the first reagent and the second reagent is 1:4, the components formulated in the first reagent may each be in a concentration in a range of 5/4 and the components formulated in the second reagent may each be in a concentration in a range of 5 folds of that of the first reagent.

In addition, a reagent which contains: a first reagent containing a protease, and an enzyme which acts on a glycated amino acid and/or a glycated peptide and which eliminates a glycated amino acid and/or a glycated peptide which are/is not generated from an N terminal of a β chain of hemoglobin; and a second reagent containing an enzyme which acts on a glycated amino acid and/or a glycated peptide and which detects a glycated amino acid and/or a glycated peptide which are/is generated from an N terminal of a β chain of hemoglobin can be formulated by: the protease reagent of the reagent not including the elimination reaction which has been added with 0.5 to 1,000 U/ml, or preferably 1.0 to 500 U/ml of the an enzyme which acts on a glycated amino acid and/or a glycated peptide and which eliminates a glycated amino acid and/or a glycated peptide which are/is not generated from an N terminal of a β chain of hemoglobin; and a reagent for glycated amino acid measurement. When a mixing ratio between the first reagent and the second reagent is not 1:1, for example, when the mixing ratio is 1:3, 1:4, 1:5, or the like, the formulation may appropriately be adjusted so that concentrations of respective components effectively function at the time of mixing. In other words, when the mixing ratio between the first reagent and the second reagent is 1:4, the components formulated in the first reagent may each be in a concentration in a range of 5/4 and the components formulated in the second reagent may each be in a concentration in a range of 5 folds of that of the first reagent.

Further, the hydrogen peroxide generated from the elimination reaction gives bad influences on a detection reaction, so the hydrogen peroxide may be decomposed by formulating a catalase and/or a peroxidase in the first reagent. The catalase may be formulated in an amount of 1 to 2,000 U/ml or preferably 5 to 1,000 U/ml, or may be formulated in other amount. Sodium azide may be formulated in a proportion of 0.001 to 0.1%, or preferably 0.02 to 0.09% in the second reagent. In addition, a peroxidase may be formulated in an amount of 0.1 to 100 U/ml, or preferably 0.2 to 50 U/ml, or may be formulated in other amount.

EXAMPLES

Hereinafter, the present invention will be described based on examples. However, the present invention is not limited to the following examples.)

Example 1

Screening of Protease Reaction Promoter (Reagent)
1) R-1: Reagent for Protein Decomposition

| | |
|---|---|
| 50 mM | Tris buffer solution (manufactured by Wako Pure Chemical Industries, Inc.), pH 7.0 |
| 4,000 U/ml | Neutral protease (manufactured by Toyobo Co., Ltd.) |
| 1.5 ml | CaCl$_2$ (manufactured by Wako Pure Chemical Industries, Inc.) |
| + | Test sample |

2) R-2: Reagent for Glycated Amino Acid Detection

| | |
|---|---|
| 50 mM | Tris buffer solution (manufactured by Wako Pure Chemical Industries, Inc.), pH 7.5 |
| 30 U/ml | KAOD (derived from Curvularia clavata YH923; manufactured by Asahi Kasei Pharma Corporation, the method of producing the same being described in JP-A-2004-275013) |
| 80 U/ml | Peroxidase (manufactured by Sigma Aldrich Japan K.K.) |
| 80 μM | DA-67 (manufactured by Wako Pure Chemical Industries, Inc.) |

The following substances were independently used as a test sample. Note that concentrations described in parentheses each represent a final concentration of the substance in the reagent R1.

Tween-20 (1%), Brij35 (1%), Triton X-100 (1%), deoxycholic acid (1%), imino-diacetic acid (IDA; 1 mM), ZnSO4 (0.1 mM), AlCl3 (0.1 mM), potassium ferrocyanide (0.01 mM), sorbitol (5%), glucose (5%), sodium nitrite (2 mM), dimethylsulfoxide (10%), adenosine 5'-triphosphate (ATP; 2 mM), nicotinamide adenine dinucleotide (NAD; 2 mM), flavin adenine dinucleotide (FAD; 2 mM) (those substances are manufactured by Wako Pure Chemical Industries, Inc.), sodium cocoyl sarcosinate (sarcosinate CN-30; 1%), sodium myristoyl sarcosinate (sarcosinate MN; 1%), sodium palmitoyl sarcosinate (sarcosinate PN; 1%), sodium lauroyl methyl alaninate (alaninate LN-30; 1%), sodium polyoxyethylene(3) tridecyl ether acetate (ECTD-3NEX; 1%), sodium polyoxyethylene(6)tridecyl ether acetate (ECTD-6NEX; 1%), polyoxyethylene(10)lauryl ether acetic acid (AKYPO-RLM100; 1%), lauryl phosphate (phosten HLP; 1%), sodium N-lauroyl methyl taurinate (LMT; 1%), sodium N-stearoyl methyl taurinate (SMT; 1%), sodium lauryl sulfate (SLS; 1%), triethanolamine polyoxyethylene(2)lauryl ether sulfate (SBL-2T-36; 1%), triethanolamine polyoxyethylene(4)lauryl ether sulfate (SBL-4T; 1%), triethanolamine polyoxyethylene(3) alkyl ether sulfate (SBL-203-27; 1%), betaine lauryl dimethylaminoacetate (AM-301; 1%), monostearate polyoxyethylene(15)glyceryl (TMGS-15; 1%), 3-[(3-cholamidopropyl)dimethyl-ammonio]propanesulfonic acid (CHAPS; 1%) (those substances are manufactured by Nikko Chemicals Co., Ltd.), and WST-3 (2 mM; manufactured by Dojindo Laboratories).

(Operation Method)

180 µl of the reagent R-1 which had been preincubated to 37° C. was added with 20 µl of a standard substance for HbA1c measurement (primary calibrator JDS HbA1c Lot2, manufactured by Health Care Technology Foundation, 30-fold diluted product) to initiate a reaction at 37° C., and 45 µl of the reagent R-2 was added thereto exactly 5 minutes after the initiation of the reaction. Absorbance before the addition of the reagent R-2 and 5 minutes after the addition was measured at 660 nm. Table 1 shows evaluation results of protease reaction promoting effects of the above-mentioned test samples. The AH-AL shown in Table 1 is a difference obtained by subtracting absorbance AL which was obtained from the primary calibrator at level 2 (5.38%) from absorbance AH which was obtained from the primary calibrator at level 4 (9.88%). Here, if AH-AL is large, the sample is judged to have a protease reaction promoting effect. In particular, when AH-AL is 20 or more, the sample has an excellent promoting effect.

As shown in Table 1, the effects were observed in the reagents containing sarcosinate CN-30, sarcosinate MN, sarcosinate PN, and alaninate LN-30 that were N-acylamino acids, ECTD-3NEX, ECTD-6NEX, and AKYPO-RLM100 that were alkyl ether carboxylates, LMT and SMT that were N-acyl taurates, and SBL-2T-36, SBL-4T, and SBL-203-27 that were polyoxyethylene alkyl ether sulfate.

From the findings, it was apparent that the acetate group-containing compound or the salt thereof, N-acyl taurine or the salt thereof, or polyoxyethylene alkyl ether sulfuric acid or the salt thereof had the protease reaction promoting effects. It was also apparent that the acetate group-containing compound or the salt thereof such as an N-acylamino acid or the salt thereof or alkyl ether carboxylic acid or the salt thereof had the protease reaction promoting effects.

It was apparent that the N-acylamino acid or the salt thereof such as a compound represented by the following general formula (1) or the salt thereof had the protease reaction promoting effect:

$$R^1-CO-R^2 \tag{1}$$

wherein $R^1$ represents an alkyl group or an alkenyl group, and $R^2$ represents a monovalent group obtained by removing a hydrogen atom from an amino group in an amino acid or an amino acid derivative. Among those, it was found that the compound in which $R^1$ represents $CH_3(CH_2)_n-$ (provided that, n represents an integer of 10 to 14) or a heptadec-8-enyl group, and/or $R^2$ represents a standard amino acid, N-methylalanine, or sarcosine is preferable.

It was apparent that the alkyl ether carboxylic acid or the salt thereof such as a compound represented by the following general formula (2) had the protease reaction promoting effect:

$$R^3-O-(CH_2-CH_2-O)_mCH_2COOM \tag{2}$$

wherein $R^3$ represents an alkyl group, m represents an integer of 3 to 10, and M represents a hydrogen atom or a metal that forms a salt with carboxylic acid. Among those, it was found that the compound in which $R^3$ represents $CH_3(CH_2)_Q-$ (provided that, Q represents 10 or 11) is preferable. Note that almost the same results were obtained when TPM-PS was used instead of DA67. In addition, addition of a saccharide did not promote the protease reaction. However, when the reagent to which sorbitol was added was used as a control, the change in absorbance of the control was 6.5 mAbs, and reaction promoting effects about 4.3 folds or larger than that of the control were observed in a case of the N-acylamino acid, alkyl ether carboxylic acid, N-acyl taurine, and polyoxyethylene alkyl ether sulfate. Note that the measurement was able to be performed when the change in absorbance of 10 mAbs or more was obtained. In this case, the reaction promoting effect was calculated to be 1.5 folds, so a reaction promoting effect of 1.5 folds or more is sufficient for the measurement.

TABLE 1

|  | Compound | Concentration in R-1 | $A_H$ | $A_L$ | $A_H - A_L$ |
|---|---|---|---|---|---|
| Neutral surfactant | Tween-20 | 1% | 88.5 | 79.2 | 9.3 |
|  | Brij35 | 1% | 232.7 | 214.3 | 18.4 |
|  | TritonX-100 | 1% | 44.9 | 39.7 | 5.2 |
| Cholic acid derivative | Deoxycholic acid | 1% | 69.0 | 62.9 | 6.1 |
|  | CHAPS | 1% | 111.4 | 104.5 | 6.9 |
| Chelating agent | IDA | 1 mM | 67.7 | 62.2 | 5.5 |
| Metallic salt | $ZnSO_4$ | 100 mM | 145.7 | 144.1 | 1.6 |
|  | $AlCl_3$ | 100 mM | 60.7 | 55.1 | 5.6 |
|  | Potassium ferrocyanide | 10 µm | 72.9 | 66.8 | 6.1 |
| Saccharide | Sorbitol | 5% | 68.3 | 61.8 | 6.5 |
|  | Glucose | 5% | 73.5 | 68.7 | 4.8 |
| Organic solvent | Dimethylsulfoxide | 10% | 63.0 | 59.6 | 3.4 |
| Co-enzyme | ATP | 2 mM | 57.8 | 54.2 | 3.6 |
|  | NAD | 2 mM | 66.3 | 63.5 | 2.8 |
|  | FAD | 2 mM | 46.2 | 45.5 | 0.7 |
| N-acylamino acid or salt thereof | Sarcosinate CN-30 | 1% | 106.2 | 76.6 | 29.6 |
|  | Sarcosinate MN | 1% | 124.2 | 95.4 | 28.8 |
|  | Sarcosinate PN | 1% | 130.5 | 102.5 | 28.0 |
|  | Alaninate LN-30 | 1% | 92.3 | 65.6 | 26.7 |
| Alkyl ether carboxylic acid or salt thereof | ECTD-3NEX | 1% | 95.8 | 68.3 | 27.5 |
|  | ECTD-6NEX | 1% | 82.9 | 53.4 | 29.5 |
|  | AKYPO-RLM100 | 1% | 77.8 | 48.7 | 29.1 |
| N-acyl taurine or | LMT | 1% | 102.4 | 73.0 | 29.4 |

TABLE 1-continued

| Compound | | Concentration in R-1 | $A_H$ | $A_L$ | $A_H - A_L$ |
|---|---|---|---|---|---|
| salt thereof | SMT | 1% | 110.2 | 86.4 | 23.8 |
| Polyoxyethylene alkyl ether sulfuric acid or salt thereof | SBL-2T-36 | 1% | 93.3 | 65.3 | 28.0 |
| | SBL-4T | 1% | 103.2 | 75.2 | 28.0 |
| | SBL-203-27 | 1% | 112.1 | 84.3 | 27.8 |
| Sulfate compound | SLS | 1% | 53.3 | 48.7 | 4.6 |
| Phosphate compound | Phosten HLP | 1% | 134.6 | 121.9 | 12.7 |
| Betaine acetic acid-type | AM-301 | 1% | 122.0 | 109.9 | 12.1 |
| Glycerin fatty acid ester | TMGS-15 | 1% | 92.0 | 82.2 | 9.8 |
| Tetrazolium salt | WST-3 | 2 mM | 184.6 | 160.9 | 23.7 |
| Nitrite salt | Sodium nitrite | 2 mM | 107.9 | 81.7 | 26.2 |

Example 2

Reagent Containing Protease Reaction Promoter (Reagent)
Reagent for Hemoglobin Measurement

| 50 mM | Tris buffer solution (manufactured by Wako Pure Chemical Industries, Inc.), pH 7.0 |
| 1% | Sarcosinate MN |
| 0.05% | Sodium azide |

Reagents as the above-mentioned reagent were also prepared separately except that AKYPO-RLM100, SMT, and SBL-2Z-36 were used, respectively, instead of sarcosinate MN.

Example 3

Reagent Containing Protease Reaction Promoter and Protease (Reagent)
1) R-1: Reagent for Protein Decomposition

| 50 mM | Tris buffer solution (manufactured by Wako Pure Chemical Industries, Inc.), pH 7.0 |
| 4,000 U/ml | Neutral protease (manufactured by Toyobo Co., Ltd.; Toyozyme NEP) |
| 1.5 ml | CaCl$_2$ (Wako Pure Chemical Industries, Inc.) |
| 1% | Alaninate LN-30 |
| 0.05% | Sodium azide |

Specificity of the protease in this reagent was confirmed using glycated valyl-histidyl-leucyl-threonyl-proline and glycated valyl-leucyl-seryl-prolyl-alanine. It was found that the protease in this reagent has high specificity to the N terminal of a β chain of hemoglobin and does not substantially act on the N terminal of an α chain thereof. Further, similar substrate specificity was observed in cases of thermolysin and thermoase (manufactured by Daiwa Kasei K.K.) derived from *Bacillus thermoproteolyticus* Rokko, protease derived from *Bacillus* sp. ASP-842 FERM BP-08641, and protease derived from *Lysobacter enzymogenes* YK366 FERM BP-10010, and any one of them was confirmed to be formulated instead of the neutral protease (manufactured by Toyobo Co., Ltd.; Toyozyme NEP).

Example 4

Reagent (for HbA1c) containing protease reaction promoter, protease, enzyme which acts on glycated amino acid and/or glycated peptide, protease stabilizer, and/or stabilizer for enzyme which acts on glycated amino acid and/or glycated peptide (Reagent)
1) R-1: Reagent for Protein Decomposition

| 50 mM | Tris buffer solution (manufactured by Wako Pure Chemical Industries, Inc.), pH 7.0 |
| 4,000 U/ml | Neutral protease (manufactured by Toyobo Co., Ltd.) |
| 1.5 ml | CaCl$_2$ (manufactured by Wako Pure Chemical Industries, Inc.) |
| 1% | Alaninate LN-30 |
| 6% | DMSO |
| 0.05% | Sodium azide |

2) R-2: Reagent for Glycated Amino Acid Detection
2-1) R-2-A

| 50 mM | Tris buffer solution (manufactured by Wako Pure Chemical Industries, Inc.), pH 7.5 |
| 60 U/ml | KAOD (derived from Curvularia clavata YH923; manufactured by Asahi Kasei Pharma Corporation, the method of producing the same being described in JP-A-2004-275013) or KAOD derived from *Neocosmospora vasinfecta* 474 strain described in WO 2004/104203 |
| 160 U/ml | Peroxidase (manufactured by Sigma Aldrich Japan K.K.) |
| 10% | Sorbitol |
| 0.1% | Sodium azide |

2-2) R-2-B

| 50 mM | Tris buffer solution (manufactured by Wako Pure Chemical Industries, Inc.), pH 7.5 |
| 160 µM | DA-67 (manufactured by Wako Pure Chemical Industries, Inc.) |

Example 5

Reagent (for HbA1c) containing protease reaction promoter, protease, enzyme which acts on glycated amino acid and/or glycated peptide, protease stabilizer, and/or stabilizer for enzyme which acts on glycated amino acid and/or glycated peptide (Reagent)
1) R-1: Reagent for Protein Decomposition

| | |
|---|---|
| 50 mM | Tris buffer solution (manufactured by Wako Pure Chemical Industries, Inc.), pH 7.0 |
| 4,000 U/ml | Neutral protease (manufactured by Toyobo Co., Ltd.) |
| 1.5 mM | CaCl$_2$ (Wako Pure Chemical Industries, Inc.) |
| 1% | Alaninate LN-30 |
| 6% | DMSO |
| 0.05% | Sodium azide |

2) R-2: Reagent for Glycated Amino Acid Detection

| | |
|---|---|
| 50 mM | Tris buffer solution (manufactured by Wako Pure Chemical Industries, Inc.), pH 7.5 |
| 60 U/ml | KAOD (derived from Curvularia clavata YH923; manufactured by Asahi Kasei Pharma Corporation, the method of producing the same being described in JP-A-2004-275013) or KAOD derived from *Neocosmospora vasinfecta* 474 strain described in WO 2004/104203 |
| 160 U/ml | Peroxidase (manufactured by Sigma Aldrich Japan K.K.) |
| 10% | Sorbitol |
| 0.1% | Sodium azide |
| 160 µM | DA-67 (manufactured by Wako Pure Chemical Industries, Inc.) |
| 2% | 2-hydroxylpropyl-β-cyclodextrin (manufactured by Nihon Shokuhin Kako Co., Ltd.) |

Example 6

Reagent including: a first reagent containing protease and enzyme which acts on glycated amino acid and/or glycated peptide and eliminates glycated amino acid and/or glycated peptide that are/is not generated from N terminal of β chain of hemoglobin; and a second reagent containing enzyme which acts on glycated amino acid and/or glycated peptide and detects glycated amino acid and/or glycated peptide that are generated from N terminal of β chain of hemoglobin
(Reagent)
1) R-1: Reagent for Protein Decomposition

| | |
|---|---|
| 50 mM | Tris buffer solution (manufactured by Wako Pure Chemical Industries, Inc.), pH 7.0 |
| 4,000 U/ml | Neutral protease (manufactured by Toyobo Co., Ltd.) |
| 1.5 mM | CaCl$_2$ (manufactured by Wako Pure Chemical Industries, Inc.) |
| 1% | Alaninate LN-30 |
| 6% | DMSO |
| 0.05% | Sodium azide |
| 10 U/ml | KAOD (manufactured by Asahi Kasei Pharma Corporation) |

2) R-2: Reagent for Glycated Amino Acid Detection

| | |
|---|---|
| 50 mM | Tris buffer solution (manufactured by Wako Pure Chemical Industries, Inc.), pH 7.5 |
| 60 U/ml | KAOD (derived from Curvularia clavata YH923; manufactured by Asahi Kasei Pharma Corporation, the method of producing the same being described in JP-A-2004-275013) |
| 160 U/ml | Peroxidase (manufactured by Sigma Aldrich Japan K.K.) |
| 10% | Sorbitol |
| 0.1% | Sodium azide |
| 160 µM | DA-67 (manufactured by Wako Pure Chemical Industries, Inc.) |
| 2% | 2-hydroxylpropyl-β-cyclodextrin (manufactured by Nihon Shokuhin Kako Co., Ltd.) |

Example 7

Reagent including: a first reagent containing enzyme which acts on glycated amino acid and/or glycated peptide; and a second reagent containing protease
(Reagent)
1) R-1: Reagent for Protein Decomposition

| | |
|---|---|
| 50 mM | Tris buffer solution (manufactured by Wako Pure Chemical Industries, Inc.), pH 7.0 |
| 12 U/ml | KAOD (derived from *Curvularia clavata* YH923; manufactured by Asahi Kasei Pharma Corporation, the method of producing the same being described in JP-A-2004-275013) |
| 32 U/ml | Peroxidase (manufactured by Sigma Aldrich Japan K.K.) |
| 6% | Sorbitol |
| 0.05% | Sodium azide |
| 32 µM | DA-67 (manufactured by Wako Pure Chemical Industries, Inc.) |
| 2% | 2-hydroxylpropyl-β-cyclodextrin (manufactured by Nihon Shokuhin Kako Co., Ltd.) |
| 1% | Alaninate LN-30 |

2) R-2: Reagent for Glycated Amino Acid Detection

| | |
|---|---|
| 50 mM | Tris buffer solution (manufactured by Wako Pure Chemical Industries, Inc.), pH 7.5 |
| 20,000 U/ml | Neutral protease (manufactured by Toyobo Co., Ltd.) |
| 1.5 mM | CaCl$_2$ (manufactured by Wako Pure Chemical Industries, Inc.) |
| 30% | DMSO |
| 0.05% | Sodium azide |

Example 8

Reagent (for GA) containing protease reaction promoter, protease, enzyme which acts on glycated amino acid and/or glycated peptide, protease stabilizer, and/or stabilizer for enzyme which acts on glycated amino acid and/or glycated peptide
1) R-1: Reagent for Protein Decomposition

| | |
|---|---|
| 50 mM | Tris buffer solution (manufactured by Wako Pure Chemical Industries, Inc.), pH 7.0 |
| 8 mM | 4-AA |
| 10% | DMSO |
| 10,000 U/ml | Protease derived from *Bacillus licheniformis* (manufactured by Sigma Aldrich Japan K.K.) (the protease was used after being subjected to purification and desalting with DEAE-sepharose resin) |
| 0.001675% | BCP (manufactured by Wako Pure Chemical Industries, Inc.) |
| 0.05% | Sodium azide |
| 0.5% | Tween20 |
| | (±1% Alaninate LN-30) |

2) R-2: Reagent for Glycated Amino Acid Detection

| | |
|---|---|
| 50 mM | Tris buffer solution (manufactured by Wako Pure Chemical Industries, Inc.), pH 7.5 |
| 5% | Sorbitol |
| 20 U/ml | KAOD (manufactured by Asahi Kasei Pharma Corporation) |
| 5 U/ml | Peroxidase (manufactured by Sigma Aldrich Japan K.K.) |
| 10 mM | N-ethyl-N-(2-hydroxy-3-sulfopropyl)-3-metylaniline•sodium salt, dihydride (TOOS; Dojindo Laboratories) |
| 0.05% | Sodium azide |

Example 9

Measurement of Hemoglobin and Stability of Reagent

By using the reagents of Example 2, measurement was performed for a standard product having a known hemoglobin concentration.
(Reaction Procedure for Reagent for Hemoglobin Measurement)
Measurement was performed by using an autoanalyzer (Hitachi autoanalyzer 7170S; manufactured by Hitachi Ltd.). 20 µl of a sample was added with 180 µl of each of the reagents, and changes in absorbance were measured at 660 nm. Water was used as a control, and differences in absorbance between the sample and the water were calculated after 5 minutes. 5-serially diluted products of the standard hemoglobin product were used as the sample.
FIG. 1 shows the results. As shown in FIG. 1, hemoglobin was able to be quantified by using the protease reaction promoters of the present invention (sarcosinate MN, AKYPO-RLM100, SMT, and SBL-2Z-36). In addition, a preservation test was performed for a reagent in which sarcosinate MN was used as a protease reaction promoter at 37° C. for 4 days. The measurement of 5.5 g/dl of the standard hemoglobin product was performed by using, as a calibrator, a 30-fold diluted product of a standard substance for HbA1c measurement (primary calibrator JDS HbA1c Lot2, manufactured by Health Care Technology Foundation, level 1, hemoglobin concentration of 135 g/L). As a result, the measurement values of the hemoglobin were 54 mAbs, 4.5 g/L before the preservation test and 50 mAbs, 4.6 g/L after the preservation test. From the results, it was assumed that the present reagent is stable for 6 months or longer under refrigeration.

Example 10

Measurement of Hemoglobin A1c and Calculation of Hemoglobin A1c Ratio

Measurement was performed using the reagents of Examples 4 and 5.
(Reagent)
1) Standard substance for HbA1c measurement (primary calibrator JDS HbA1c Lot2, manufactured by Health Care Technology Foundation), 30-fold diluted product
2) Chyle-contaminated hemoglobin which was obtained by adding 1 volume of chyle (2,000 degree, interference check; manufactured by Sysmex Corporation) to 9 volumes of the 30-fold diluted product of the primary calibrator JDS HbA1c Lot2
(Preparation of R-2 Reagent)
The R-2-A reagent and the R-2-B reagent of Example 4 were mixed before use in a proportion of 1:1. The reagents of Example 5 were used as they are.
(Reaction Procedure for Reagent for Hemoglobin A1c Measurement)
Measurement was performed by using an autoanalyzer (Hitachi autoanalyzer 7170S; manufactured by Hitachi Ltd.). 20 µl of the sample was added with 180 µl of the R-1 reagent, and the whole was incubated to 37° C., and then changes in absorbance were measured by using a dominant wavelength of 660 nm and a subwavelength of 700 nm. After 5 minutes, 45 µl of the R-2 reagent was added thereto, and the whole was incubated to 37° C., and then changes in absorbance were measured by using a dominant wavelength of 660 nm and a subwavelength of 700 nm. In addition, obtained values were converted into measurement values by using the standard substance for HbA1c measurement (primary calibrator JDS HbA1c Lot2, manufactured by Health Care Technology Foundation, level 1; hemoglobin concentration of 135 g/L, HbA1c value of 4.04% and level 5; hemoglobin concentration of 132 g/L, HbA1c value of 12.63%) as a calibrator. The hemoglobin was quantified by photometry immediately before the addition of the R-2 reagent, and the HbA1c was quantified by photometry 5 minutes after the addition of the R-2 reagent.
FIGS. 2 and 3 show calibration curves of the hemoglobin and the HbA1c, respectively. The HbA1c concentration was calculated from HbA1c % and an Hb concentration of the standard substance for HbA1c measurement. As apparent from FIG. 2, the hemoglobin A1c was able to be quantified by using the protease reaction promoter of the present invention. In addition, as apparent from FIG. 3, the hemoglobin was also able to be quantified using the same. From the findings, it was apparent that the hemoglobin and HbA1c were able to be sequentially measured in the same reaction vessel by using the present invention.
In addition, when the subwavelength was not subtracted in the measurement of the chyle-contaminated hemoglobin, the absorbance which was calculated at the time when the reagent and the R-1 were mixed, and reproducibility was 3.5% in CV when measurement was performed 5 times with the primary calibrator JDS HbA1c Lot2 of level 1 with an HbA1c value of 4.04%. On the other hand, when the subwavelength was subtracted, the reproducibility was 1.5% and accuracy increased. From the findings, it was apparent that the HbA1c was able to be accurately measured by measuring the hemoglobin and the HbA1c at the same wavelengths, and subtracting values obtained with subwavelength. In addition, the same results were obtained by using ketoamine oxidases derived from *Curvularia clavata* YH923 (manufactured by Asahi Kasei Pharma Corporation, the method of producing the same being described in JP-A-2004-275013) and derived from *Neocosmospora vasinfecta* 474 strain described in WO 2004/104203.
Further, the reagents R-1 and R-2-A were preserved at 37° C. for 4 days in liquid states to evaluate stability thereof. Note that the reagent R-2-B of Example 4 was preserved under refrigeration, and the reagents R-2-A and R-2-B were mixed immediately before use. As the results of the measurement, the hemoglobin quantitative values of the 30-fold diluted product of the primary calibrator JDS HbA1c Lot2 of level 3 (hemoglobin concentration of 145 g/L, HbA1c value of 7.32%) were as follows: the reagent of Example 4 had 58 mAbs, 4.8 g/L and the reagent of Example 5 had 55 mAbs, 4.8 g/L before the preservation test; and the reagent of Example 4 had 56 mAbs, 4.7 g/L and the reagent of Example 5 had 54 mAbs, 4.7 g/L before the preservation test. In addition, the calculated values for the HbA1c were as follows: the reagent of Example 4 had 7.5% and the reagent of Example 5 had 7.6% before the preservation test; and the reagent of Example 4 had 7.6% and the reagent of Example 5 had 7.5% after the preservation test. In addition, no difference was observed in the measurement values in data obtained preservation for 3 months under refrigeration. From the results, it was assumed that the reagents R-1 and R-2-A of Example 4 and the reagents in Example 5 were stable for 6 months or longer under refrigeration. In general, a leuco-type colorant has high reactivity while being unstable. Therefore, the leuco-type colorant had to be preserved in isolation from other components in the reagents of Example 4. However, it was apparent that the leuco-type colorant was stabilized by the addition of a cyclodextrin, and thus was able to be formulated in the same container together with the other components.

In addition, the reagents of Examples 4 and 5 employed enzymes each of which is characterized by, as a protease, cleaving substantially no glycated amino acid and/or glycated peptide from a glycated N terminal of an α chain of glycated hemoglobin or a fragment thereof, and by allowing a protease that cleaves a glycated amino acid and/or a glycated peptide form a glycated N terminal of a β chain thereof to act on the glycated amino acid and/or the glycated peptide, the enzyme having a higher action on glycated varyl-histidine than that for glycated varyl-leucine. The quantitative values of JDS HbA1c Lot 2 at level 3 for the reagents corresponded to the indicated value. Therefore, it was apparent that the reagents accurately measured the hemoglobin A1c.

Example 11

Performance of Reagent Incorporated with Elimination System (Reagent)
The reagents of Examples 6 and 7 were used.
(Sample)
9 volumes of a 30-fold diluted product of a standard substance for HbA1c measurement (primary calibrator JDS HbA1c Lot2, level 3 (HbA1c value of 7.32%), manufactured by Health Care Technology Foundation) was added with 1 volume of a glycated amino acid to prepare a sample. In addition, for a control, the 30-fold diluted product to which distilled water was added instead of the glycated amino acid was used. Concentrations of the added glycated amino acids were as follows: a glycated Z-lysine solution (FZL) had a concentration of 2 mM and a glycated valine solution (FV) had a concentration of 2 mM, the glycated amino acids being synthesized and purified according to the method of Hashiba et. al. (Hashiba H, J. Agric Food Chem. 24: 70, 1976).
(Reaction Procedure)
The samples were subjected to measurement according to the same procedure as in Example 10.

As the results of the measurement, in a case of using the reagents of Example 6, the HbA1c quantitative values of the primary calibrator JDS HbA1c Lot2 at level 3 (HbA1c value of 7.32%) were 7.2, 7.3 and 7.1% for the control, the FZL-added sample, and the FV-added sample, respectively. The HbA1c quantitative values were 7.3, 7.4, and 7.1%, respectively, when the reagents of Example 7 were used. It was confirmed that an elimination reaction was performed and accurate values were measured.

Example 12

Measurement of Glycated Albumin, Calculation of Ratio of Glycated Albumin, and Stability of Reagent (Reaction Procedure for Reagent for Glycated Albumin Measurement)
The reagents of Example 5 were used. 240 μl of the reagent R-1 which had been incubated to 37° C. was added with 8 μl of a control plasma H (manufactured by BML Inc.); prepared according to usage and diluted in 5 serial manner with distilled water, and absorbance thereof was measured using a dominant wavelength of 546 nm and a subwavelength of 700 nm. A reaction was initiated at 37° C., and 80 μl of the R-2 reagent was added to the mixture exactly 5 minutes after the initiation. Absorbance before the addition of the R-2 reagent and after 5 minutes of the addition was measured. In addition, measurement was performed for a blank which was prepared by using distilled water instead of the substrate solution. The change in absorbance obtained from the control substrate solution was subtracted by the change in absorbance obtained from the blank sample, to thereby calculate ΔA0. Conversion of the values was performed by simultaneous measurement for a calibrator (manufactured by Asahi Kasei Pharma Corporation) for Lucica GA and comparison of absorbance. The measurement value for albumin was obtained from a difference in absorbance which was obtained by subtracting absorbance immediately before the addition of the R-2 reagent from absorbance immediately after the addition of the sample. The measurement value for the glycated albumin was obtained from a difference in absorbance which was obtained by subtracting absorbance immediately before the addition of the R-2 reagent from absorbance after 5 minutes of the addition of the R-2 reagent.

When the sample contained no protease reaction promoter (Alaninate LN-30), the reaction of the protease was slow and sensitivity of the GA measurement of the control serum (manufactured by BML Inc.; no dilution) was 32 mAbs, which was 66% of that in a case where the sample contained the protease reaction promoter (48 mAbs). The reaction rate was increased to 1.5 folds.

In additions, FIG. 4 shows measurement values of the controlled serum which had been diluted in 5 serial manner. As shown in FIG. 4, albumin and glycated albumin were able to be quantified in the same reaction vessel at the same wavelength by using the present regents, and glycated albumin value (%) was able to be measured in a favorable manner.

Further, the present reagents were preserved at 37° C. for 4 days in liquid states. As a result, measurement of the control serum (manufactured by BML Inc.; no dilution) confirmed that sensitivity for the GA measurement was 48 mAbs, sensitivity for the albumin measurement was 60 mAbs, and a GA value was 44.8% while, after the preservation, the sensitivity for the GA measurement was 46 mAbs, the sensitivity for the albumin measurement was 61 mAbs, and the GA value was 44.5%. From the results, it was assumed that the present reagents were stable for 6 months or longer under refrigeration.

Example 13

Screening of Stabilizer for Colorant which is Used for Detection of Enzymatic Reaction (Reagent)
1) R-1: Colorant-Containing Reagent

| | |
|---|---|
| 200 mM | Tris buffer solution (manufactured by Wako Pure Chemical Industries, Inc.), pH 7.5 |
| 200 μM | DA64, DA67, or 0.04% MBTH (manufactured by Wako Pure Chemical Industries, Inc.) |
| + | Test sample |

2) R-2: Peroxidase-Containing Reagent

| | |
|---|---|
| 200 mM | Tris buffer solution (manufactured by Wako Pure Chemical Industries, Inc.), pH 7.5 |
| 10 U/ml | Peroxidase (manufactured by Sigma Aldrich Japan K.K.) |
| 0.04% | TOOS (manufactured by Wako Pure Chemical Industries, Inc.; provided that, TOOS was added only when MBTH was used in the reagent R-1) |

The following substances were used as test samples. Note that concentrations described in parentheses each represent a final concentration of the substance in the reagent R-1.

Tween-20 (1%), Brij35 (1%), Triton X-100 (1%), deoxycholic acid (1%), imino-diacetic acid (IDA; 1 mM), ZnSO4 (0.1 mM), AlCl3 (0.1 mM), potassium ferrocyanate (0.01 mM), sorbitol (5%), glucose (5%), sodium nitrite (2 mM), dimethylsulfoxide (DMSO; 10%) (those substances are manufactured by Wako Pure Chemical Industries, Inc.), 2-hydroxypropyl-β-cyclodextrin (2HP β CD; 0.5%, 2%, 5%) and methyl-β-cyclodextrin (M β CD; 0.5%, 2%, 5%) (those substances are manufactured by Nihon Shokuhin Kako Co., Ltd.).

(Operation Method)

500 μl of the R-1 reagent and 500 μl of the R-2 which had been incubated to 37° C. were mixed. The mixture was incubated to 37° C. for 2 minutes, and absorbance thereof (A0) was measured. The mixture was added with 10 μl of 500 μM hydrogen peroxide or distilled water. The whole was incubated to 37° C., and absorbance exactly 5 minutes after the addition of hydrogen peroxide (A1) was measured, to calculate a change in absorbance ΔA (A1-A0). The absorbance was measured using a wavelength of 750 nm when DA64 was used as the colorant, a wavelength of 660 nm when DA67 was used as the colorant, and a wavelength of 570 nm when 4-AA-TOOS was used as the colorant.

Immediately after the preparation of the reagent, the reagent was preserved at 37° C. for 2 days and 9 days, and measurement of sensitivity of a blank which was distilled water and of hydrogen peroxide was performed.

Tables 2-1 and 2-2 show relationship of preservation of the blank and the colorants used in the detection of the enzymatic reaction. As shown in Tables 2-1 and 2-2, a metallic salt, 2-hydroxypropyl-β-cyclodextrin, and methyl-β-cyclodextrin were confirmed to have suppressing effects on the blank. In addition, Table 3 shows the relationship of preservation of the colorants and a metallic salt and the colorant and cyclodextrin concentration when 500 μM of hydrogen peroxide was measured. With the metallic salt, an increase of blank was not observed as shown in Table 2-2-. However, as shown in Table 3, the sensitivity of hydrogen oxide itself was lost. In addition, as shown in Table 3, the stabilizing effect on the colorant was observed when a cyclodextrin had a concentration of 0.5% or more.

TABLE 2-1

Unit Abs

| Colorant | The number of preservation day(s) | Without additive | Neutral surfacant | | | Cholic acid derivative | Chelating agent |
|---|---|---|---|---|---|---|---|
| | | | Tween-20 | Brij35 | TrotonX-100 | Deoxycholic acid | IDA |
| DA-64 | 0 | −0.009 | −0.008 | −0.009 | −0.005 | −0.006 | −0.010 |
| | 2 | 0.070 | 0.075 | 0.070 | 0.080 | 0.074 | 0.078 |
| | 9 | 0.205 | 0.210 | 0.203 | 0.221 | 0.203 | 0.210 |
| DA-67 | 0 | 0.089 | 0.092 | 0.091 | 0.085 | 0.093 | 0.089 |
| | 2 | 2.566 | 2.665 | 2.464 | 2.100 | 2.351 | 2.131 |
| | 9 | — | — | — | — | — | — |
| MBTH-TOOS | 0 | 0.145 | 0.141 | 0.152 | 0.146 | 0.148 | 0.151 |
| | 2 | 1.245 | 1.235 | 1.1 | 1.135 | 1.209 | 1.213 |
| | 9 | — | — | — | — | — | — |

TABLE 2-2

Unit Abs

| Colorant | The number of preservation day(s) | Without additive | Metallic salt | | | Saccharide | Organic solvent | Cyclodextrin | |
|---|---|---|---|---|---|---|---|---|---|
| | | | ZnSO4 | AlCl3 | Potassium ferrocyanide | Sorbitol | DMSO | 2HPβCD | MβCD |
| DA-64 | 0 | −0.009 | −0.005 | −0.003 | −0.010 | −0.010 | −0.005 | −0.007 | −0.01 |
| | 2 | 0.070 | −0.001 | 0.002 | −0.005 | 0.080 | 0.085 | 0.007 | 0.005 |
| | 9 | 0.205 | 0.003 | 0.006 | −0.001 | 0.230 | 0.233 | 0.010 | 0.006 |
| DA-67 | 0 | 0.089 | 0.051 | 0.035 | 0.045 | 0.093 | 0.088 | 0.119 | 0.133 |
| | 2 | 2.566 | 0.062 | 0.072 | 0.082 | 2.545 | 2.103 | 0.762 | 0.657 |
| | 9 | — | 0.050 | 0.055 | 0.072 | — | — | 1.822 | 1.430 |
| MBTH-TOOS | 0 | 0.145 | 0.050 | 0.045 | 0.059 | 0.151 | 0.149 | 0.166 | 0.115 |
| | 2 | 1.245 | 0.049 | 0.055 | 0.062 | 1.225 | 1.134 | 0.815 | 0.757 |
| | 9 | — | 0.055 | 0.058 | 0.065 | — | — | — | — |

TABLE 3

| Colorant | The number of preservation day(s) | Without additive | Metallic salt | | | Cyclodextrin | | | | | |
|---|---|---|---|---|---|---|---|---|---|---|---|
| | | | ZnSO4 | AlCl3 | Potassium ferrocyanide | 2HPβCD | | | MβCD | | |
| | | | | | | 0.5% | 2.0% | 5.0% | 0.5% | 2.0% | 5.0% |
| DA-64 | 0 | 0.385 | −0.005 | −0.003 | −0.010 | 0.375 | 0.386 | 0.385 | 0.371 | 0.376 | 0.365 |
| | 2 | 0.224 | −0.001 | 0.002 | −0.005 | 0.315 | 0.322 | 0.326 | 0.302 | 0.309 | 0.315 |
| | 9 | 0.195 | 0.003 | 0.006 | −0.001 | 0.251 | 0.269 | 0.271 | 0.266 | 0.271 | 0.273 |
| DA-67 | 0 | 0.533 | 0.005 | 0.002 | 0.003 | 0.531 | 0.522 | 0.528 | 0.516 | 0.519 | 0.515 |
| | 2 | 0.199 | 0.001 | 0.002 | 0.003 | 0.301 | 0.306 | 0.309 | 0.355 | 0.361 | 0.364 |
| | 9 | 0.000 | 0.005 | 0.006 | 0.008 | 0.277 | 0.279 | 0.281 | 0.306 | 0.311 | 0.323 |
| MBTH-TOOS | 0 | 0.200 | 0.003 | 0.005 | 0.007 | 0.199 | 0.200 | 0.203 | 0.175 | 0.18 | 0.181 |
| | 2 | 0.110 | 0.003 | 0.009 | 0.009 | 0.145 | 0.155 | 0.159 | 0.135 | 0.136 | 0.145 |
| | 9 | — | — | — | — | — | — | — | — | — | — |

Example 14

Effect of Catalase Addition on Reagent Containing a Cyclodextrin and Colorant Used for Detection of Enzymatic Reaction (Reagent)
1) R-1: Colorant-Containing Reagent

| | |
|---|---|
| 200 mM | Tris buffer solution (manufactured by Wako Pure Chemical Industries, Inc.), pH 7.5 |
| 200 μl | DA-67 (manufactured by Wako Pure Chemical Industries, Inc.) |
| 2% | 2-hydroxypropyl-β-cyclodextrin (manufactured by Nihon Shokuhin Kako Co., Ltd.) |
| ±500 U/ml | Catalase (manufactured by Wako Pure Chemical Industries, Inc.) |

2) R-2: Peroxidase-Containing Reagent

| | |
|---|---|
| 200 mM | Tris buffer solution (manufactured by Wako Pure Chemical Industries, Inc.), pH 7.5 |
| 10 U/ml | Peroxidase (manufactured by Sigma Aldrich Japan K.K.) |
| 0.05% | Sodium azide (manufactured by Wako Pure Chemical Industries, Inc.) |

(Operation Method)

The same operation method as in Example 13 was used. Immediately after the preparation of the reagent, the reagent was preserved at 37° C. for 2 days and 9 days, and measurement of sensitivity of a blank which was distilled water and of hydrogen peroxide was performed. Table 4 shows the results. As shown in Table 4, the blank after preservation significantly decreased owing to the addition of catalase, and the stability of the colorant used in the detection of an enzymatic reaction increased.

TABLE 4

| Colorant | The number of preservation day(s) | Blank | | 500 μM hydrogen peroxide | |
|---|---|---|---|---|---|
| | | Without additive | 500 U/ml catalase | Without additive | 500 U/ml catalase |
| DA-67 | 0 | 0.119 | 0.057 | 0.522 | 0.510 |
| | 2 | 0.762 | 0.452 | 0.306 | 0.335 |
| | 9 | 1.822 | 1.052 | 0.279 | 0.304 |

Example 15

Effect of Buffer Concentration on Reagent Containing a Cyclodextrin and Colorant Used for Detection of Enzymatic Activity (Reagent)
1) R-1: Colorant-Containing Reagent

| | |
|---|---|
| 50 mM, 80 mM, 100 mM, and 200 mM | Tris buffer solution (manufactured by Wako Pure Chemical Industries, Inc.), pH 7.5 |
| 10 μM | DA67 (manufactured by Wako Pure Chemical Industries, Inc.) |
| 2% | 2-hydroxypropyl-β-cyclodextrin (manufactured by Nihon Shokuhin Kako Co., Ltd.) |
| 4,000 U/ml | Toyozyme NEP (manufactured by Toyobo Co., Ltd.) |
| 500 U/ml | Catalase (manufactured by Wako Pure Chemical Industries, Inc.) |
| 1% | Sarcosinate LN (manufactured by Nikko Chemicals Co., Ltd.) |

2) R-2: Peroxidase-Containing Reagent

| | |
|---|---|
| 50 mM | Tris buffer solution (manufactured by Wako Pure Chemical Industries, Inc.), pH 7.5 |
| 78 U/ml | Peroxidase (manufactured by Sigma Aldrich Japan K.K.) |
| 26 U/ml | KAOD derived from *Curvularia clavata* YH923 (manufactured by Asahi Kasei Pharma Corporation, the method of producing the same being described in JP-A-2004-275013) |
| 0.05% | Sodium azide (manufactured by Wako Pure Chemical Industries, Inc.) |

(Operation Method)

Measurement was performed by using an autoanalyzer (Hitachi autoanalyzer 7170S; manufactured by Hitachi Ltd.). 20 μl of the sample was added with 180 μl of the reagent R-1 and then the whole was incubated to 37°. Changes in absorbance were measured using a dominant wavelength of 660 nm and a subwavelength of 700 nm. After 5 minutes, 45 μl of the reagent R-2 was added thereto and the whole was incubated to 37°. Changes in absorbance were measured using a dominant wavelength of 660 nm and a subwavelength of 700 nm. In addition, a 30-fold diluted product of a standard substance for HbA1c measurement (primary calibrator JDS HbA1c Lot2, manufactured by Health Care Technology Foundation, level 1; 135 g/L, 4.04%, and level 5; 132 g/L, 12.36%) was used as a sample.

Immediately after the preparation of the reagent, the reagent was preserved at 37° C. for 2 days, 4 days, and 6 days, and measurement of sensitivity from level 5 to level 1 was calculated.

Table 5 shows the results. As shown in Table 5, the stability of the colorant which was used in the detection of the enzymatic reaction significantly increased when the buffer had a concentration of 80 mM or less.

TABLE 5

|  | ΔA(mAbs) | | | |
| --- | --- | --- | --- | --- |
|  | 50 mM | 80 mM | 100 mM | 200 mM |
| 0 days | 92.3 | 88.9 | 85.5 | 86.1 |
| 2 days | 95.2 | 90.2 | 86.9 | 83.8 |
| 4 days | 97.5 | 89.1 | 71.9 | 66.1 |
| 6 days | 95.3 | 88.7 | 57.6 | 30.2 |

Example 16

Reagent (for HbA1c) Containing Cyclodextrin and Colorant Used for Detection of Enzymatic Reaction (Reagent)
1: R-1: Colorant-Containing Reagent

| 50 mM | Tris buffer solution (manufactured by Wako Pure Chemical Industries, Inc.), pH 7.5 |
| --- | --- |
| 10 μl | DA-67 (manufactured by Wako Pure Chemical Industries, Inc.) |
| 2% | 2-hydroxypropyl-β-cyclodextrin (manufactured by Nihon Shokuhin Kako Co., Ltd.) |
| 4,000 U/ml | Toyozyme NEP (manufactured by Toyobo Co., Ltd.) |
| 500 U/ml | Catalase (manufactured by Wako Pure Chemical Industries, Inc.) |
| 1% | Sarcosinate LN (manufactured by Nikko Chemicals Co., Ltd.) |

2) R-2: Peroxidase-Containing Reagent

| 50 mM | Tris buffer solution (manufactured by Wako Pure Chemical Industries, Inc.), pH 7.5 |
| --- | --- |
| 78 U/ml | Peroxidase (manufactured by Sigma Aldrich Japan K.K.) |
| 26 U/ml | KAOD derived from *Curvularia clavata* YH923 (manufactured by Asahi Kasei Pharma Corporation, the method of producing the same being described in JP-A-2004-275013) |
| 0.05% | Sodium azide (manufactured by Wako Pure Chemical Industries, Inc.) |

Example 17

Reagent (for GA) Containing Cyclodextrin and Colorant Used for Detection of Enzyme Reaction 1) R-1: Reagent for Protein Decomposition

| 50 mM | Tris buffer solution (manufactured by Wako Pure Chemical Industries, Inc.), pH 7.0 |
| --- | --- |
| 10 μM | DA67 (manufactured by Wako Pure Chemical Industries, Inc.) |
| 2% | 2-hydroxypropyl-β-cyclodextrin (manufactured by Nihon Shokuhin Kako Co., Ltd.) |
| 10% | DMSO |
| 10,000 U/ml | Protease derived form *Bacillus licheniformis* (manufactured by Sigma Aldrich Japan K.K.) (the protease was used after being subjected to purification and desalting with DEAE-sepharose resin) |
| 500 U/ml | Catalase (manufactured by Wako Pure Chemical Industries, Inc.) |

2) R-2: Reagent for Glycated Amino Acid Detection

| 50 mM | Tris buffer solution (manufactured by Wako Pure Chemical Industries, Inc.), pH 7.5 |
| --- | --- |
| 5% | Sorbitol |
| 20 U/ml | KAOD (manufactured by Asahi Kasei Pharma Corporation) |
| 5 U/ml | Peroxidase (manufactured by Sigma Aldrich Japan K.K.) |
| 0.05% | Sodium azide |

Example 18

Measurement of Hemoglobin A1c, Calculation of Ratio of Hemoglobin A1c, and Stability of Reagent Measurement was performed using the reagents of Example 16.
1) Standard substance for HbA1c measurement (primary calibrator JDS HbA1c Lot2, manufactured by Health Care Technology Foundation), a 30-fold diluted product
(Reaction Procedure for Reagent for Hemoglobin A1c Measurement)

Measurement was performed by using an autoanalyzer (Hitachi autoanalyzer 7170S; manufactured by Hitachi Ltd.). 20 μl of the sample was added with 180 μl of the R-1 reagent, and the whole was incubated to 37° C. 5 minutes after the addition of the sample, 45 μl of the R-2 reagent was added thereto, and the whole was incubated to 37° C. for 5 minutes. Changes in absorbance were measured immediately before the addition of the R-2 reagent (A1) and 5 minutes after the addition (A2) at a dominant wavelength of 660 nm and a subwavelength of 700 nm. In addition, obtained values were converted into measurement values by using a standard substance for HbA1c measurement (primary calibrator JDS HbA1c Lot2, manufactured by Health Care Technology Foundation, level 1, hemoglobin concentration of 135 g/L, HbA1c value 4.04% and level 5; hemoglobin concentration 132 g/L, HbA1c value 12.63%) as a calibrator. The hemoglobin and the HbA1c were quantified through calculation using A1 and A2-A1, respectively.

FIGS. 5 and 6 show calibration curves of hemoglobin and HbA1c, respectively. As shown in FIGS. 5 and 6, the hemoglobin A1c and the hemoglobin were able to be quantified by using the method of stabilizing the colorant used for the detection of the enzyme reaction of the present invention. It was apparent that, since the hemoglobin A1c and the hemoglobin were able to be quantified, the ratio of the hemoglobin A1c was able to be calculated.

Further, the present reagent was preserved at 37° C. for 4 days in a liquid state. As a result, the 30-fold diluted product of the primary calibrator JDS HbA1c Lot2 at level 3 (hemoglobin concentration of 145 g/L, HbA1c value 7.32%) had a hemoglobin quantitative values of 40 mAbs, 4.8 g/L before the preservation test and 38 mAbs, 4.7 g/L after the preservation test. In addition, the calculated values of HbA1c were 7.2% before the preservation test and 7.3% after the preservation test. In addition, no difference was observed in the measurement values in data obtained preservation for 3 months under refrigeration. From the results, it was assumed that the present reagent was stable for 6 months or longer under refrigeration.

Example 19

Measurement of Glycated Albumin, Calculation of Ratio of Glycated Albumin, and Stability of Reagent (Reaction Procedure for Reagent for Glycated Albumin Measurement)

The same reagents as in Example 17 were used. 240 µl of the R-1 reagent which had been incubated to 37° C. was added with 8 µl of a control serum H (manufactured by BML Inc.; prepared according to usage and diluted in 5 serial manner with distilled water). A reaction was initiated at 37° C., and 80 µl of the R-2 reagent was added to the mixture exactly 5 minutes after the initiation. Absorbance before the addition of the R-2 reagent and after 5 minutes of the addition was measured at a dominant wavelength of 660 nm and a subwavelength of 700 nm. In addition, measurement was performed for a blank which was prepared by using distilled water instead of the substrate solution. The change in absorbance obtained from the control substrate solution was subtracted by the change in absorbance obtained from the blank sample, to thereby calculate ΔA0. Conversion of the values was performed by simultaneous measurement for a calibrator (manufactured by Asahi Kasei Pharma Corporation) for Lucica GA and comparison of absorbance. The measurement of albumin was performed by using Aquaauto Kaonos ALB reagent (manufactured by Kainos, Inc.) in an amount based on the usage amount of the reagent. FIG. 7 shows the measurement values of the controlled serum which had been diluted in 5 serial manner. As shown in FIG. 7, albumin and glycated albumin were quantified using the present reagent, and the glycated albumin value (%) was measured in a favorable manner.

Further, the present reagent was preserved at 37° C. for 4 days in a liquid state. As a result, measurement of the controlled serum L (manufactured by BML Inc.; no dilution) confirmed that sensitivity for the GA measurement was 150 mAbs and a GA value was 18.3% while, after the preservation, the sensitivity for the GA measurement was 146 mAb and the GA value was 18.2%. From the results, it was assumed that the present reagent was stable for 6 months or longer under refrigeration.

INDUSTRIAL APPLICABILITY

The reagent for measurement and the measurement method of the present invention are used in clinical laboratory tests.

BRIEF DESCRIPTION OF THE DRAWINGS

FIG. 1 shows results of measurement of hemoglobin according to Example 9 of the present invention.

FIG. 2 shows results of measurement of hemoglobin A1c according to Example 10 of the present invention.

FIG. 3 shows results of measurement of hemoglobin according to Example 10 of the present invention.

FIG. 4 shows results of measurement of glycated albumin according to Example 12 of the present invention.

FIG. 5 shows a calibration curve of hemoglobin A1c according to Example 18 of the present invention.

FIG. 6 shows a calibration curve of hemoglobin according to Example 18 of the present invention.

FIG. 7 shows results of measurement of glycated albumin according to Example 19 of the present invention. In the figure, a closed square indicates an albumin concentration, a closed rhomboid indicates a glycated albumin concentration, and a closed triangle indicates a glycated albumin value.

The invention claimed is:

1. A method for stabilizing a kit of compositions comprising a first composition and a second composition used for the measurement of glycated hemoglobin or glycated albumin in a sample comprising:

making a protease, 10-(carboxymethylaminocarbonyl)-3,7-bis(dimethylamino)phenothiazine, and a cyclodextrin coexist together in the absence of a sample containing glycated hemoglobin or glycated albumin, and thereby providing the first composition comprising the protease, 10-(carboxymethylaminocarbonyl)-3,7-bis(dimethylamino)phenothiazine, and the cyclodextrin with no sample containing glycated hemoglobin or glycated albumin, and providing the second composition containing an oxidase which oxidizes a glycated amino acid and/or a glycated peptide, wherein the first and second compositions of the kit remain stable in a liquid state for 6 months or longer under refrigeration in the absence of a sample containing glycated hemoglobin or glycated albumin.

2. The method according to claim 1, wherein the cyclodextrin is a β-cyclodextrin.

3. The method according to claim 1, wherein the first composition containing the protease, 10-(carboxymethylaminocarbonyl)-3,7-bis(dimethylamino)phenothiazine, and the cyclodextrin further comprises a buffer in a concentration of 100 mM or less.

4. The method according to claim 3, wherein the first composition containing the protease, 10-(carboxymethylaminocarbonyl)-3,7-bis(dimethylamino)phenothiazine, and the cyclodextrin further comprises a buffer in a concentration of 80 mM or less.

5. A method of measuring glycated hemoglobin or glycated albumin in a blood sample, comprising:

adding to the blood sample, the first composition stabilized by the method according to claim 1, thus providing a mixture of the blood sample and the first composition, adding to the mixture the second composition according to claim 1, and detecting through the activity of the oxidase which oxidizes a glycated amino acid and/or a glycated peptide, the presence of glycated amino acids and/or glycated peptides cleaved from glycated hemoglobin or glycated albumin present in the blood sample.

6. The method according to claim 5, wherein the cyclodextrin is a β-cyclodextrin.

7. The method according to claim 5, wherein the first composition containing the protease, 10-(carboxymethylaminocarbonyl)-3,7-bis(dimethylamino)phenothiazine, and the cyclodextrin further comprises a buffer in a concentration of 100 mM or less.

8. The method according to claim 7, wherein the first composition containing the protease, 10-(carboxymethylaminocarbonyl)-3,7-bis(dimethylamino)phenothiazine, and the cyclodextrin further comprises a buffer in a concentration of 80 mM or less.

\* \* \* \* \*